US008065119B2

(12) United States Patent
Gard et al.

(10) Patent No.: US 8,065,119 B2
(45) Date of Patent: Nov. 22, 2011

(54) COMPUTERIZED METHOD AND SYSTEM FOR DESIGNING AN AERODYNAMIC FOCUSING LENS STACK

(75) Inventors: Eric Gard, San Francisco, CA (US); Vincent Riot, Oakland, CA (US); Keith Coffee, Diablo Grande, CA (US); Bruce Woods, Livermore, CA (US); Herbert Tobias, Kensington, CA (US); Jim Birch, Albany, CA (US); Todd Weisgraber, Brentwood, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 691 days.

(21) Appl. No.: 12/052,597

(22) Filed: Mar. 20, 2008

(65) Prior Publication Data

US 2008/0221842 A1 Sep. 11, 2008

Related U.S. Application Data

(62) Division of application No. 11/471,093, filed on Jun. 19, 2006, now Pat. No. 7,361,891.

(60) Provisional application No. 60/691,521, filed on Jun. 17, 2005, provisional application No. 60/714,689, filed on Sep. 6, 2005.

(51) Int. Cl.
*G06F 17/50* (2006.01)

(52) U.S. Cl. ................................................ 703/2; 703/1

(58) Field of Classification Search ........................ None
See application file for complete search history.

(56) References Cited

U.S. PATENT DOCUMENTS 5,015,845 A 5/1991 Allen et al.
5,270,542 A 12/1993 McMurry et al.
5,439,513 A 8/1995 Periasamy et al.
5,481,357 A 1/1996 Ahsan et al.
5,565,677 A 10/1996 Wexler et al.
6,032,513 A 3/2000 Chorush et al.
6,348,687 B1 2/2002 Brockmann et al.

(Continued)

OTHER PUBLICATIONS

Liu et al, Generating Particle Beams of Controlled Dimensions and Divergence: I. Theory of Particle Motion in Aerodynamic Lenses and Nozzle Expansions, Aerosol Science and Technology 22:293-313, 1995.*

(Continued)

*Primary Examiner* — Robert Kim
*Assistant Examiner* — Andrew Smyth
(74) *Attorney, Agent, or Firm* — James S. Tak

(57) ABSTRACT

A computerized method and system for designing an aerodynamic focusing lens stack, using input from a designer related to, for example, particle size range to be considered, characteristics of the gas to be flowed through the system, the upstream temperature and pressure at the top of a first focusing lens, the flow rate through the aerodynamic focusing lens stack equivalent at atmosphere pressure; and a Stokes number range. Based on the design parameters, the method and system determines the total number of focusing lenses and their respective orifice diameters required to focus the particle size range to be considered, by first calculating for the orifice diameter of the first focusing lens in the Stokes formula, and then using that value to determine, in iterative fashion, intermediate flow values which are themselves used to determine the orifice diameters of each succeeding focusing lens in the stack design, with the results being output to a designer. In addition, the Reynolds numbers associated with each focusing lens as well as exit nozzle size may also be determined to enhance the stack design.

10 Claims, 11 Drawing Sheets

U.S. PATENT DOCUMENTS

| | | | | |
|---|---|---|---|---|
| 6,454,862 | B1 * | 9/2002 | Yoshida et al. | 118/722 |
| 6,827,761 | B2 | 12/2004 | Graham | |
| 6,906,322 | B2 | 6/2005 | Berggren et al. | |
| 7,476,851 | B2 * | 1/2009 | Wang et al. | 250/288 |
| 2004/0021015 | A1 * | 2/2004 | Murdoch | 239/533.12 |
| 2005/0073683 | A1 | 4/2005 | Gard et al. | |
| 2005/0197809 | A1 * | 9/2005 | Dowski et al. | 703/6 |
| 2006/0065869 | A1 * | 3/2006 | Chipman et al. | 251/118 |
| 2006/0102837 | A1 * | 5/2006 | Wang et al. | 250/288 |
| 2008/0022853 | A1 * | 1/2008 | Ariessohn | 95/267 |

OTHER PUBLICATIONS

Zhang et al., Numerical Characterization of Particle Beam Collimation: Part II Integrated Aerodynamic-Lens-Nozzle System, Aerosol Science and Technology, 38:619-638, 2004.*

Schreiner et al. “Focusing of Aerosols into a Particle Beam at Pressures from 10 to 150 Torr” 1999 Aerosol Science and Technology 31:373-382.

Liu et al. “Generating Particle Beams of Controlled Dimensions and Divergence: I. Theory of Particle Motion in Aerodynamic Lenses and Nozzle Expansions” 1995 Aerosol Science and Technology 22:293-313.

Zhang et al. “A Numerical Characterization of Particle Beam Collimation bu an Aerodynamic Lens-Nozzle System: Part I. An Individual Lens or Nozzle” 2002 Aerosol Science and Technology 36:617-631.

Wang et al. “A Design Tool for Aerodynamic Lens Systems” 2006 Aerosol Science and Technology 40:320-334.

* cited by examiner

COMPUTERIZED METHOD AND SYSTEM FOR DESIGNING AN AERODYNAMIC FOCUSING LENS STACK

CROSS-REFERENCE TO RELATED APPLICATIONS

This application is a divisional of prior application Ser. No. 11/471,093 filed Jun. 19, 2006 now U.S. Pat. No. 7,361,891, entitled "Pressure-Flow Reducer for Aerosol Focusing Devices" by Eric E. Gard et al, which claims the benefit of provisional application No. 60/691,521, filed on Jun. 17, 2005, entitled "Pressure-Flow Reducer for Aerosol Focusing Devices" by Eric E. Gard et al, and provisional application No. 60/714,689, filed on Sep. 6, 2005, entitled "Design Tool for Aerodynamic Focusing Lens Stacks" by Vincent J. Riot et al, all of which are incorporated by reference herein.

FEDERALLY SPONSORED RESEARCH OR DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to aerosol focusing systems, and more particularly to an aerosol focusing system having a pressure flow reducer which couples a sampling inlet operating at atmosphere pressure into vacuum incorporating focusing lens stack technology to achieve a high sampling rate.

BACKGROUND OF THE INVENTION

Aerosol characterizing instruments generally require highly focused particle beams with little or no transmission losses. In addition, they need to interface to the sampling environment with a very high sampling rate so that more aerosol particles can be collected and sensitivity can be improved. Aerodynamic focusing lens stacks have been shown to generate highly focused aerosol particle beam into vacuum, and have been used effectively for various aerosol studies [1]. Current focusing lens stacks, however, operate on small particle diameters [4] and at low pressure and low flow rate. By design, aerodynamic focusing lens stacks for aerosol particles in the range of 0.5 um to 10 um can only operate at low flow rate and low pressure due to the low Reynolds numbers required for each focusing lens in order to maintain laminar flow within the lens stack. And the orifice sizes have to be kept below one centimeter and above 100 um in order to be machined with acceptable tolerances and aligned in an inlet system. As such, the low pressure and low flow rate make it fairly difficult to interface aerodynamic focusing lens stacks with an aerosol source at atmosphere pressure. Traditionally, single critical orifice devices have been used to interface lens stacks to the atmospheric pressure environment, where the dimensions of the orifices are defined by the pressure required by the lens stack. Due to the coupling between pressure and flow rate however, critical orifices yield a very poor sampling efficiency when the sampling flow is less than 0.05 L/min, resulting in a very small number of particles transmitted through the entire system.

What is needed therefore is an aerosol focusing system (AFS) having a large-particle focusing inlet with a high sampling rate that is capable of interfacing between atmosphere pressure and vacuum where aerosol mass-spectrometry analysis may be performed [7]. In particular an aerosol focusing system design is needed that incorporates aerodynamic lens stack focusing technology with high flow atmospheric pressure sampling and delivers a tightly focused particle beam in vacuum within, for example, 300 μm for particles ranging from 1 μm to 10 μm. Furthermore, what is also needed is a design tool for dimensioning and validating the AFS (including various components of the AFS individually, such as the lens stack) so that various interface systems could be designed rapidly for different operating conditions without the need of lengthy computational fluid dynamic and costly bench top experimentation.

SUMMARY OF THE INVENTION

One aspect of the present invention includes a pressure-flow reducer apparatus for use with an aerosol focusing device characterized by an operating pressure, said apparatus comprising: an inlet nozzle for drawing particle-laden air from a sampling environment characterized by a sampling pressure greater than the operating pressure of the aerosol focusing device; a skimmer having an orifice aligned with and spaced downstream from the inlet nozzle to form a gap between the skimmer and the inlet nozzle; a pumping port in fluidic communication with the gap for reducing the pressure and flow from the inlet nozzle; and a relaxation chamber downstream of and in fluidic communication with the skimmer orifice and having an outlet capable of fluidically connecting to the aerosol focusing device, for reducing the velocity of particles entering from the skimmer orifice before exiting out to the aerosol focusing device.

Another aspect of the present invention includes an aerosol focusing system comprising: an aerosol focusing device characterized by an operating pressure and having an exit nozzle; and a pressure-flow reducer apparatus upstream of said aerosol focusing device, and comprising: an inlet nozzle for drawing particle-laden air from a sampling environment characterized by a sampling pressure greater than the operating pressure of the aerosol focusing device; a skimmer having an orifice aligned with and spaced downstream from the inlet nozzle to form a gap between the skimmer and the inlet nozzle; a pumping port in fluidic communication with the gap for reducing the pressure and flow from the inlet nozzle; and a relaxation chamber downstream of and in fluidic communication with the skimmer orifice and having an outlet capable of fluidically connecting to the aerosol focusing device, for reducing the velocity of particles entering from the skimmer orifice before exiting out to the aerosol focusing device.

Another aspect of the present invention includes a computerized method for designing an aerodynamic focusing lens stack, said computerized method comprising: receiving as input in a computer the design parameters of: (1) the particle size range to be considered ($d_{particle\ (min)}$, $d_{particle\ (max)}$) and the particle density thereof ($\rho_{particle}$); (2) characteristics of the gas to be flowed through the aerodynamic focusing lens stack design, including dynamic viscosity (μ), standard gas mean free path ($\lambda_{standard}$), heat ratio (γ), gas constant (R), molecular mass (M), and flow type, either isothermal flow or isentropic flow; (3) the temperature (T[1]) and pressure (P[1]) upstream of a first focusing lens [i=1] of the aerodynamic focusing lens stack design; (4) the flow rate through the aerodynamic focusing lens stack equivalent at atmosphere pressure ($Q_{equ}$); and (5) a Stokes number range defining the focusing tightness ($Stk_{min}$, $Stk_{max}$); based on said received design parameters, determining the number of focusing lenses and their respective orifice diameters ($d_{lens}[i]$) required to focus the particle size range to be considered, and including the steps of. (a) solving for the orifice diameter ($d_{lens}[i]$) of the $i^{th}$ focusing lens, in the Stokes number equation: FOCUS(T[i], Q[i], P[i], $\lambda_{standard}$, μ, $d_{lens}[i]$, $d_{particle}[i]$, $\rho_{particle}$, $Stk_{max}$)=0, beginning with the first focusing lens [i=1] where $d_{particle}[1]=d_{particle\ (max)}$ and $$Q[1] = Q_{equ}\left(\frac{P_{atm}}{P[1]}\right);$$

(b) using the value of the orifice diameter ($d_{lens}[i]$) in step (a) to solve for a new maximum particle size $d_{particle}[i+1]$ to be focused in the next $[i+1]^{th}$ focusing lens, in the Stokes number equation: FOCUS(T[i], Q[i], P[i], $\lambda_{standard}$, μ, $d_{lens}[i]$, $d_{particle}[i+1]$, $\rho_{particle}$, $Stk_{min}$)=0; (c) determining the pressure drop across the $[i]^{th}$ focusing lens by solving for a pressure P[i+1] downstream of the $[i]^{th}$ focusing lens and upstream of the next $[i+1]^{th}$ focusing lens, in the Prandtl derivation: DROP(T[i], Q[i], P[i], P[i+1], $d_{lens}[i]$, γ, R, M)=0; (d) setting the temperature T[i+1] and flow rate Q[i+1] of the next $[i+1]^{th}$ focusing lens according to: if the flow type is isothermal flow, then T[i+1]=T[i] and $$Q[i+1] = Q[i]\left(\frac{P[i]}{P[i+1]}\right) = Q_{equ}\left(\frac{P_{atm}}{P[i+1]}\right);$$

and if the flow type is isentropic flow, then $$T[i+1] = T[i]\left(\frac{P[i+1]}{P[i]}\right)^{\frac{\gamma-1}{\gamma}}$$

and $$Q[i+1] = Q[i]\left(\frac{P[i]}{P[i+1]}\right) = Q_{equ}\left(\frac{P_{atm}}{P[i+1]}\right)^{\frac{1}{\gamma}};$$

and (e) setting i=i+1 and iteratively performing steps (a) through (d) using the values for $d_{particle}[i+1]$, P[i+1], T[i+1], and Q[i+1] determined in the previous iteration, until $d_{particle}[i+1]$ in step (b) is less than $d_{particle\ (min)}$; and outputting to a designer the respective orifice diameters of all the number of focusing lens determined to be required to focus the particle size range to be considered.

Another aspect of the present invention includes a computerized method for designing an aerodynamic focusing lens stack, said computerized method comprising: receiving as input in a computer the design parameters of: (1) the particle size range to be considered ($d_{particle\ (min)}$, $d_{particle\ (max)}$) and the particle density thereof ($\rho_{particle}$); (2) characteristics of the gas to be flowed through the aerodynamic focusing lens stack design, including dynamic viscosity (μ), standard gas mean free path ($\lambda_{standard}$) heat ratio (γ), gas constant (R), molecular mass (M), and flow type, either isothermal flow or isentropic flow; (3) the temperature (T[1]) and pressure (P[1]) upstream of a first focusing lens [i=1] of the aerodynamic focusing lens stack design; (4) the flow rate through the aerodynamic focusing lens stack equivalent at atmosphere pressure ($Q_{equ}$); and (5) a Stokes number range defining the focusing tightness ($Stk_{min}$, $Stk_{max}$); based on said received design parameters, determining the number of focusing lenses and their respective orifice diameters ($d_{lens}[i]$) required to focus the particle size range to be considered, and including the steps of: (a) solving for the orifice diameter ($d_{lens}[i]$) of the $i^{th}$ focusing lens, in the Stokes number equation: FOCUS(T[i], Q[i], P[i], $\lambda_{standard}$, μ, $d_{lens}[i]$, $d_{particle}[i]$, $\rho_{particle}$, $Stk_{max}$)=0, beginning with the first focusing lens [i=1] where $d_{particle}[1]=d_{particle\ (max)}$ and $$Q[1] = Q_{equ}\left(\frac{P_{atm}}{P[1]}\right);$$

(b) using the value of the orifice diameter ($d_{lens}[i]$) in step (a) to solve for a new maximum particle size $d_{particle}[i+1]$ to be focused in the next $[i+1]^{th}$ focusing lens, in the Stokes number equation: FOCUS(T[i], Q[i], P[i], $\lambda_{standard}$, μ, $d_{lens}[i]$, $d_{particle}[i+1]$, $\rho_{particle}$, $Stk_{min}$)=0; (c) determining the pressure drop across the $[i]^{th}$ focusing lens by solving for a pressure P[i+1] downstream of the $[i]^{th}$ focusing lens and upstream of the next $[i+1]^{th}$ focusing lens, in the Prandtl derivation: DROP(T[i], Q[i], P[i], P[i+1], $d_{lens}[i]$, γ, R, M)=0; (d) setting the temperature T[i+1] and flow rate Q[i+1] of the next $[i+1]^{th}$ focusing lens according to: if the flow type is isothermal flow, then T[i+1]=T[i] and $$Q[i+1] = Q[i]\left(\frac{P[i]}{P[i+1]}\right) = Q_{equ}\left(\frac{P_{atm}}{P[i+1]}\right);$$

and if the flow type is isentropic flow, then $$T[i+1] = T[i]\left(\frac{P[i+1]}{P[i]}\right)^{\frac{\gamma-1}{\gamma}}$$

and $$Q[i+1] = Q[i]\left(\frac{P[i]}{P[i+1]}\right) = Q_{equ}\left(\frac{P_{atm}}{P[i+1]}\right)^{\frac{1}{\gamma}};$$

and (e) setting i=i+1 and iteratively performing steps (a) through (d) using the values for $d_{particle}[i+1]$, P[i+1], T[i+1], and Q[i+1] determined in the previous iteration, until $d_{particle}[i+1]$ in step (b) is less than $d_{particle\ (min)}$; determining the flow stability through each focusing lens of the aerodynamic focusing lens stack design by solving for the Reynolds number (Re[i]) in the formula:

$$Re[i] = \left(\frac{Q[i]\cdot d_{lens}[i]}{1000\cdot 60\cdot \pi\cdot\left(\frac{d_{lens}[i]}{2}\right)^2}\right)\left(\frac{\rho}{\mu}\right),$$

where ρ is the density of the gas; determining the orifice diameter of an exit nozzle of the aerodynamic focusing lens stack design operating in a choked mode to lock the operating pressure and flow, by solving for the orifice diameter ($d_{exitnozzle}$) of the exit nozzle in the Prandtl formula:

$$Q_{exitnozzle} = \pi\left(\frac{d_{exitnozzle}}{2}\right)^2\cdot\sqrt{\frac{R_0T_{top}}{M}}\cdot\sqrt{\gamma\left(\frac{2}{\gamma+1}\right)^{\frac{\gamma+1}{\gamma-1}}},$$

where $Q_{exitnozzle}$ is estimated using the formula $$Q_1 = Q_2 \cdot \frac{P_2}{P_1}$$

for the pressure downstream of the last focusing lens, and the pressure downstream of the last focusing lens is itself determined from the final iteration of step (c); and outputting to a designer the respective orifice diameters of all the number of focusing lens determined to be required to focus the particle size range to be considered, the respective Reynolds numbers of all the number of focusing lens; and the orifice diameter of the exit nozzle.

Another aspect of the present invention includes a computer system for designing an aerodynamic focusing lens stack, said computer system comprising: input means for receiving the design parameters of: (1) the particle size range to be considered ($d_{particle\ (min)}$, $d_{particle\ (max)}$); particle density of the particle size range to be considered ($\rho_{particle}$); (2) characteristics of the gas to be flowed through the aerodynamic focusing lens stack design, including dynamic viscosity ($\mu$), standard gas mean free path ($\lambda_{standard}$), heat ratio ($\gamma$), gas constant (R), molecular mass (M), and flow type, either isothermal flow or isentropic flow; (3) the temperature (T[1]) and pressure (P[1]) immediately upstream of a first focusing lens [i=1] of the aerodynamic focusing lens stack design; (4) a flow rate through the aerodynamic focusing lens stack equivalent at atmosphere pressure ($Q_{equ}$); and (5) a Stokes number range defining the focusing tightness ($Stk_{min}$, $Stk_{max}$); computer processor means for determining, based on said received design parameters, the number of focusing lenses and their respective orifice diameters ($d_{lens}$[i]) required to focus the particle size range to be considered, said computer processor means for determining adapted to: (a) solve for the orifice diameter ($d_{lens}$[i]) of the $i^{th}$ focusing lens, in the Stokes number equation: FOCUS(T[i], Q[i], P[i], $\lambda_{standard}$, $\mu$, $d_{lens}$[i], $d_{particle}$[i], $\rho_{particle}$, $Stk_{max}$)=0, beginning with the first focusing lens [i=1] where $d_{particle}$[1]=$d_{particle\ (max)}$ and $$Q[1] = Q_{equ}\left(\frac{P_{atm}}{P[1]}\right);$$

(b) use the value of the orifice diameter ($d_{lens}$[i]) in step (a) to solve for a new maximum particle size $d_{particle}$[i+1] to be focused in the next $[i+1]^{th}$ focusing lens, in the Stokes number equation: FOCUS(T[i], Q[i], P[i], $\lambda_{standard}$, $\mu$, $d_{lens}$[i], $d_{particle}$[i+1], $\rho_{particle}$, $Stk_{min}$)=0; (c) determine the pressure drop across the $[i]^{th}$ focusing lens by solving for a pressure P[i+1] downstream of the $[i]^{th}$ focusing lens and upstream of the next $[i+1]^{th}$ focusing lens, in the Prandtl derivation: DROP(T[i], Q[i], P[i], P[i+1], $d_{lens}$[i], $\gamma$, R, M)=0; (d) set the temperature T[i+1] and flow rate Q[i+1] of the next $[i+1]^{th}$ focusing lens according to: if the flow type is isothermal flow, then $$T[i+1] = T[i] \text{ and } Q[i+1] = Q[i]\left(\frac{P[i]}{P[i+1]}\right) = Q_{equ}\left(\frac{P_{atm}}{P[i+1]}\right);$$

and if the flow type is isentropic flow, then $$T[i+1] = T[i]\left(\frac{P[i+1]}{P[i]}\right)^{\frac{\gamma-1}{\gamma}}$$

and $$Q[i+1] = Q[i]\left(\frac{P[i]}{P[i+1]}\right) = Q_{equ}\left(\frac{P_{atm}}{P[i+1]}\right)^{\frac{1}{\gamma}};$$

and (e) set i=i+1 and iteratively performing steps (a) through (d) using the values for $d_{particle}$[i+1], P[i+1], T[i+1], and Q[i+1] determined in the previous iteration, until $d_{particle}$[i+1] in step (b) is less than $d_{particle\ (min)}$; and output means for communicating to a designer the number of focusing lenses and their respective orifice diameters ($d_{lens}$[i]) determined to be required to focus the particle size range to be considered.

Another aspect of the present invention includes a computer program product comprising: a computer useable medium and computer readable code embodied on said computer useable medium for causing the automatic determination of an optimal aerodynamic focusing lens stack design based on a set of design parameters, said computer readable code comprising: computer readable program code means for causing a computer to receive as input the following design parameters: (1) the particle size range to be considered ($d_{particle\ (min)}$), $d_{particle\ (max)}$); particle density of the particle size range to be considered ($\rho_{particle}$); (2) characteristics of the gas to be flowed through the aerodynamic focusing lens stack design, including dynamic viscosity ($\mu$), standard gas mean free path ($\lambda_{standard}$), heat ratio ($\gamma$), gas constant (t), molecular mass (M), and flow type, either isothermal flow or isentropic flow; (3) the temperature (T[1]) and pressure (P[1]) immediately upstream of a first focusing lens [i=1] of the aerodynamic focusing lens stack design; (4) a flow rate through the aerodynamic focusing lens stack equivalent at atmosphere pressure ($Q_{equ}$); and (5) a Stokes number range defining the focusing tightness ($Stk_{min}$, $Stk_{max}$); computer readable program code means for causing the computer to determine, based on said received design parameters, the number of focusing lenses and their respective orifice diameters ($d_{lens}$[i]) required to focus the particle size range to be considered, by: (a) solving for the orifice diameter ($d_{lens}$[i]) of the $i^{th}$ focusing lens, in the Stokes number equation: FOCUS (T[i], Q[i], P[i], $\lambda_{standard}$, $\mu$, $d_{lens}$[i], $d_{particle}$[i], $\rho_{particle}$, $Stk_{max}$)=0, beginning with the first focusing lens [i=1] where $d_{particle}$[1]=$d_{particle\ (max)}$ and $$Q[1] = Q_{equ}\left(\frac{P_{atm}}{P[1]}\right);$$

(b) using the value of the orifice diameter ($d_{lens}$[i]) in step (a) to solve for a new maximum particle size $d_{particle}$[i+1] to be focused in the next $[i+1]^{th}$ focusing lens, in the Stokes number equation: FOCUS(T[i], Q[i], P[i], $\lambda_{standard}$, $\mu$, $d_{lens}$[i], $d_{particle}$[i+1], $\rho_{particle}$, $Stk_{min}$)=0; (c) determining the pressure drop across the $[i]^{th}$ focusing lens by solving for a pressure P[i+1] downstream of the $[i]^{th}$ focusing lens and upstream of the next $[i+1]^{th}$ focusing lens, in the Prandtl derivation: DROP(T[i], Q[i], P[i], P[i+1], $d_{lens}$[i], $\gamma$, R, M)=0; (d) setting the temperature T[i+1] and flow rate Q[i+1] of the next $[i+1]^{th}$ focusing lens according to: if the flow type is isothermal flow, then $$T[i+1] = T[i] \text{ and } Q[i+1] = Q[i]\left(\frac{P[i]}{P[i+1]}\right) = Q_{equ}\left(\frac{P_{atm}}{P[i+1]}\right);$$

and if the flow type is isentropic flow, then $$T[i+1] = T[i]\left(\frac{P[i+1]}{P[i]}\right)^{\frac{\gamma-1}{\gamma}}$$

and $$Q[i+1] = Q[i]\left(\frac{P[i]}{P[i+1]}\right) = Q_{equ}\left(\frac{P_{atm}}{P[i+1]}\right)^{\frac{1}{\gamma}};$$

and (e) setting i=i+1 and iteratively performing steps (a) through (d) using the values for $d_{particle}$[i+1], P[i+1], T[i+1], and Q[i+1] determined in the previous iteration, until $d_{particle}$ [i+1] in step (b) is less than $d_{particle\ (min)}$; and computer readable program code means for outputting to a designer the number of focusing lenses and their respective orifice diameters ($d_{lens}$[i]) determined to be required to focus the particle size range to be considered.

BRIEF DESCRIPTION OF THE DRAWINGS

The accompanying drawings, which are incorporated into and form a part of the disclosure, are as follows.

DETAILED DESCRIPTION

A. Aerosol Focusing System

The aerosol focusing system ("AFS") of the present invention incorporates aerodynamic lens stack focusing technology with high-flow, atmospheric-pressure sampling and delivers a tightly focused particle beam in vacuum within, for example, 300 μm for particles ranging from 1 μm to 10 μm, which for bio-aerosol studies corresponds to organisms that are more likely deposited in the human lung. This is achieved by using a pressure-flow reducer (PFR) instead of a critical orifice, in conjunction with two other main parts of the AFS: an aerosol focusing device, such as an aerodynamic focusing lens stack, and an exit nozzle of the aerosol focusing device.

Figure 1:
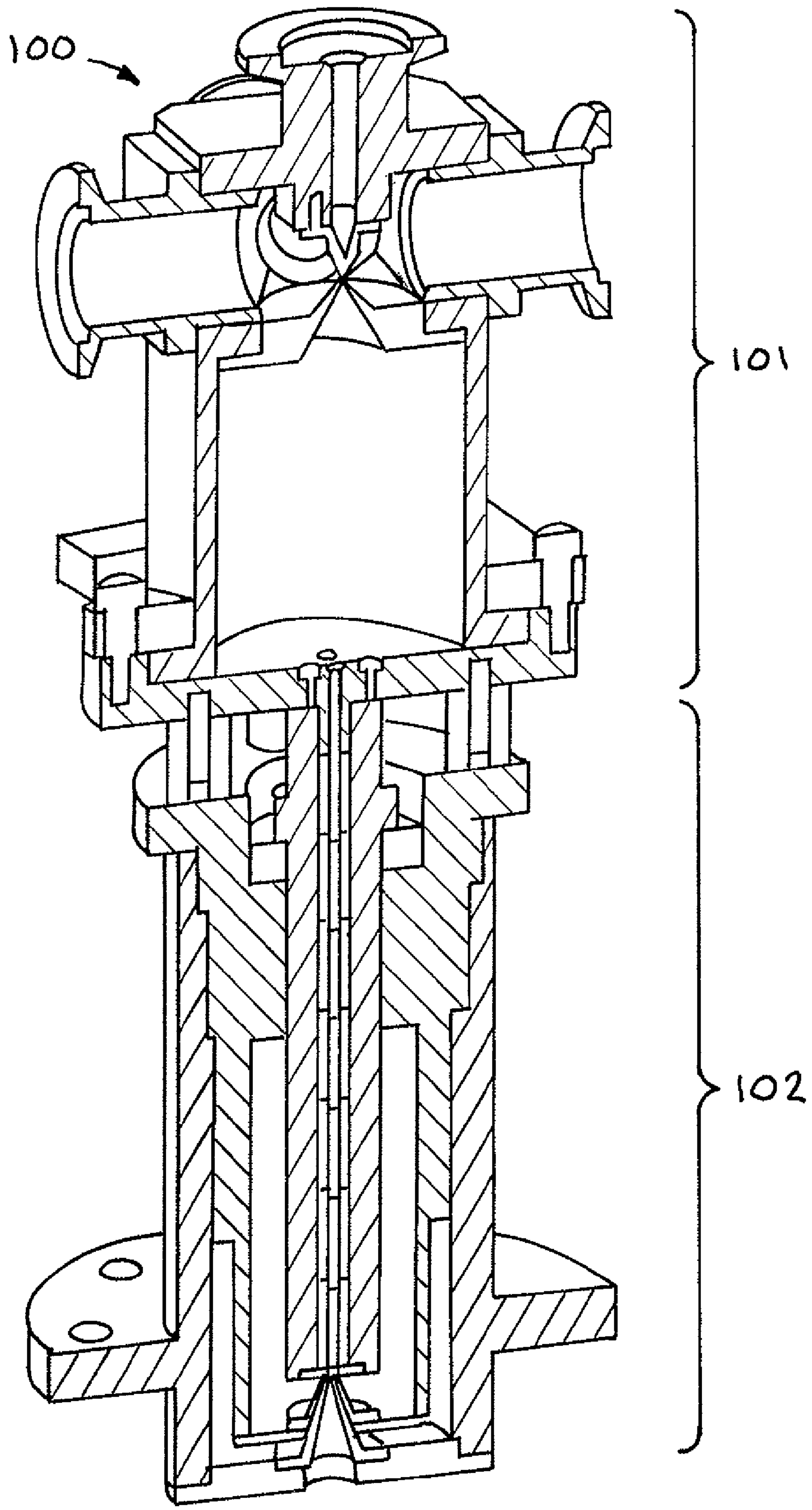
FIG. 1 is a 3-D cross-sectional view of an exemplary embodiment of the aerosol focusing system (AFS) of the present invention comprising a pressure-flow reducer and an aerosol focusing lens stack.
Figure 3:
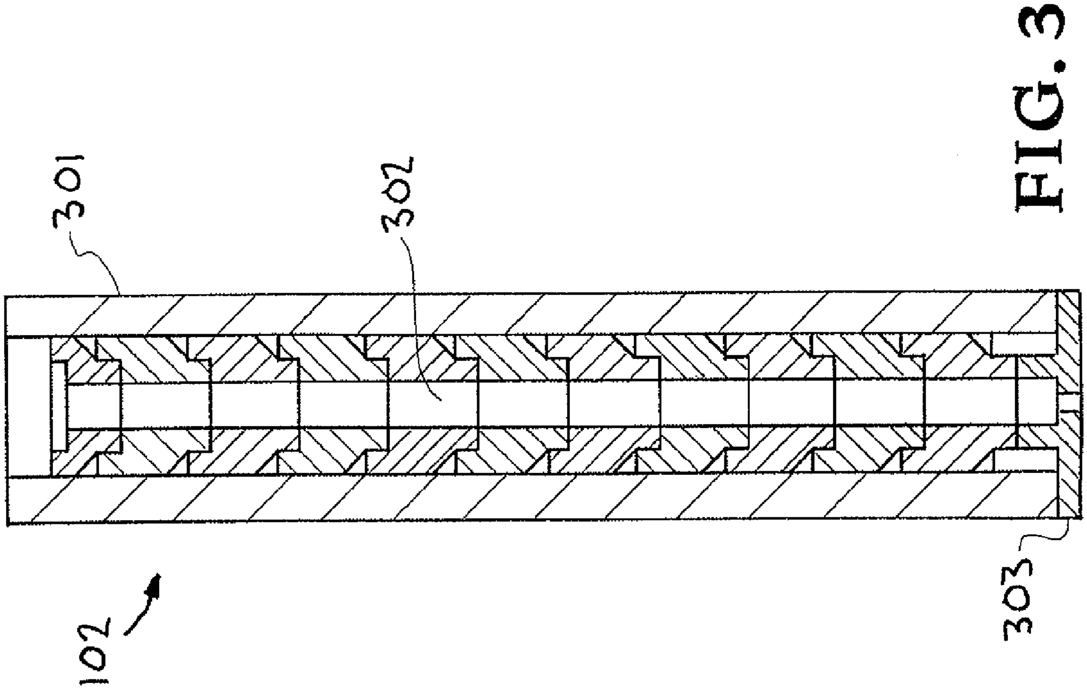
FIG. 3 is a cross-sectional view of the lens stack assembly 102 shown in FIG. 1.
Figure 2:
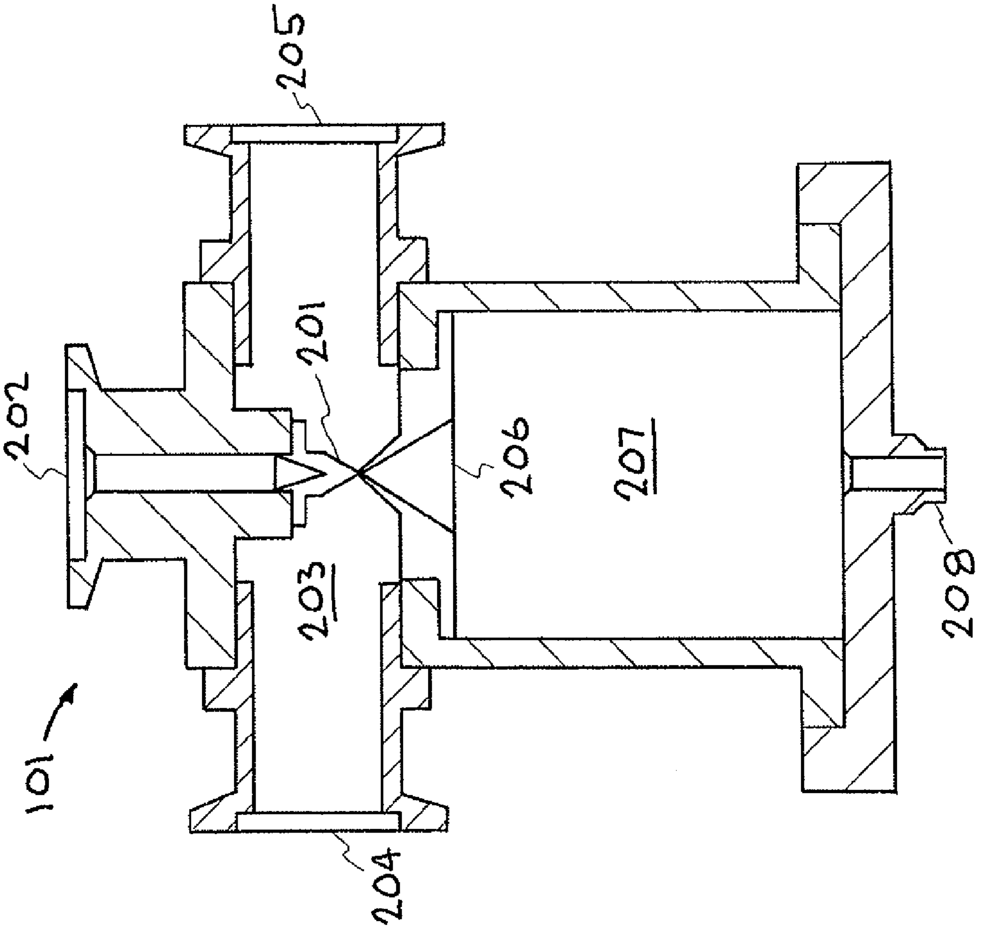
FIG. 2 is a cross-sectional view of the pressure-flow reducer 101 shown in FIG. 1.

Turning now to the drawings, FIG. 1 shows a 3-D cross-sectional view of an exemplary AFS of the present invention, generally indicated at reference character 100, having a PFR 101 and an aerodynamic focusing lens stack 102, downstream of and aligned with the PFR. FIG. 2 shows a cross-sectional view of the PFR 102 and its component sections. And FIG. 3 shows a cross-section view of just the lens stack having an exit nozzle at a downstream end. Each of these three AFS components and their design will be discussed in greater detail below. Additionally, the present invention provides a method of designing the AFS, i.e. dimensioning and validating the AFS including various components of the AFS individually, such as the lens stack, so that various interface systems could be designed rapidly for different operating conditions without the need of lengthy computational fluid dynamic and costly bench top experimentation. In particular, an analytical design methodology is used to design the three main parts of the AFS, including the focusing lens stack, the PFR for high-flow sampling at atmospheric pressure and the final exit nozzle.

B. Pressure Flow Reducer

The first component of the AFS of the present invention is the pressure-flow reducer (PFR) based on a sampling nozzle and a skimmer, used to interface a focusing lens stack to atmosphere pressure and high flow rate with minimum losses. Generally, the constraints imposed by the low Reynolds numbers within the lens stack have the tendency to limit designs operating parameters to low initial pressure and flow rate [4]. This is a drawback for aerosol collecting systems that would naturally operate at atmosphere pressure. In addition, the low flow rate reduces the amount of aerosol particles that can be collected per unit of time thus reducing the sensitivity of any type of analysis instrument using this type of inlet. The PER is an apparatus that enables the interfacing of high pressure and high flow sampling conditions to a low pressure low flow operating focusing lens stack.

Generally, the PFR device is an aerosol inlet that interfaces between an aerosol sample (generally at a pressure of 760

Torr with a flow rate greater than a liter per minute) and an aerosol focusing device operating at low pressure and low flow rate (typically 10 to 100 Torr at 0.05 liter per minute) such as aerodynamic focusing lens stacks. And in particular, the PFR makes use of a nozzle for adjusting the sampling flow rate, a pumped region with a skimmer for reducing the pressure and flow to accommodate the aerosol focusing device and finally a relaxation chamber for slowing or stopping the aerosol particles. The pressure-flow reducer technology decouples pressure from flow by incorporating a pumping stage, allowing aerosol sampling at atmospheric pressure and at rates greater than 1 Liter per minutes. This yields sampled particle concentrations per unit time that are 20 times greater than traditional. Thus, the system allows for a high particle transmission efficiency and aerosol concentration into any aerosol focusing device, and in particular, making aerodynamic lens stack focusing technology practical for the sampling of low concentration aerosols at higher pressure environments.

FIG. 2 shows a PFR 101 having three stages which work in conjunction with the exit nozzle size of an aerosol focusing device such as the aerodynamic focusing lens stack 102 shown in FIG. 3. The stack exit nozzle, although not part of PFR system, governs the configuration of the PFR and must be taken into account for proper design and operation of the technology.

Figure 4:
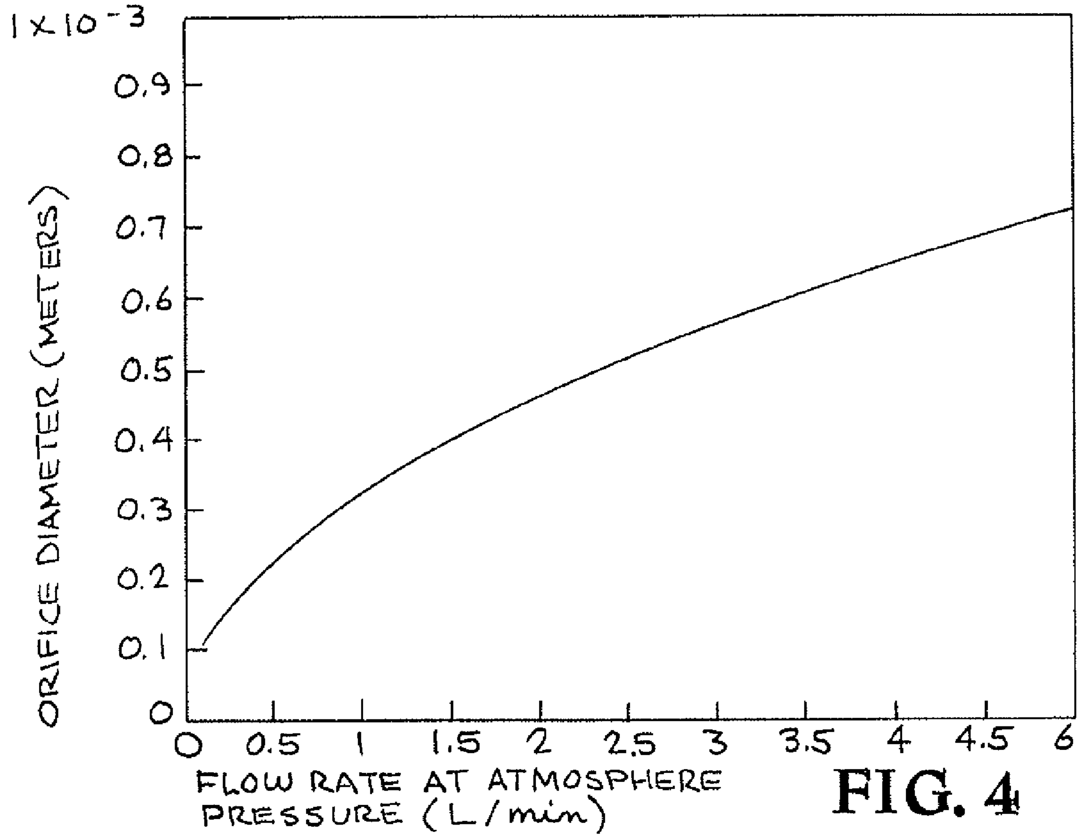
FIG. 4 is a graph showing inlet nozzle orifice diameter in relation to flow rate for a sampling pressure of 760 Torr.

The first stage of the PFR 101 in FIG. 2 consists of an inlet nozzle 201 drawing air from the sampling environment, via inlet 202. The pressure of the sampling environment, referred to as the sampling pressure, is typically one atmosphere (760 Torr). The pressure below the PFR is defined as the operating pressure of the aerosol focusing device. The PFR will operate properly as long as the sampling pressure is at least twice that of the operating pressure thereby choking the inlet flow and producing a supersonic jet accelerating the aerosol particles to speeds around 300 m/s. Because of the supersonic expansion through the inlet nozzle 201, the sampling pressure and flow are solely defined by the size of the inlet nozzle orifice, regardless of the pressure below, as long as the pressure below is at least half of the sampling pressure. FIG. 4 shows the relation between inlet nozzle diameter and flow rate if the sampling pressure is set to one atmosphere. The purpose of the first stage is to define the aerosol sampling flow regardless of the operating conditions of the aerosol focusing device (such as a focusing lens stack).

The second stage of the PFR 101 in FIG. 2 is the reduction chamber 203 formed by a skimmer 206 and a pumping port or ports, such as 204 and 205. This stage, in conjunction with the aerosol focusing device exit nozzle dimensions, allows reduction of flow and pressure so that it matches the aerosol focusing device requirements. The pumping port(s) must be connected to a vacuum pump (not shown) whose pumping capacity can be varied (using a choking mechanism such as a valve). It is appreciated that a single pumping port may be used. Or in the alternative, pumping can be split over several distributed ports for a m-ore uniform pressure distribution within the chamber. The pumping efficiency, skimmer diameter and distance from the inlet nozzle are defined by the pressure that the aerosol focusing device requires and set the particle transmission efficiency throughout the system.

Figure 5:
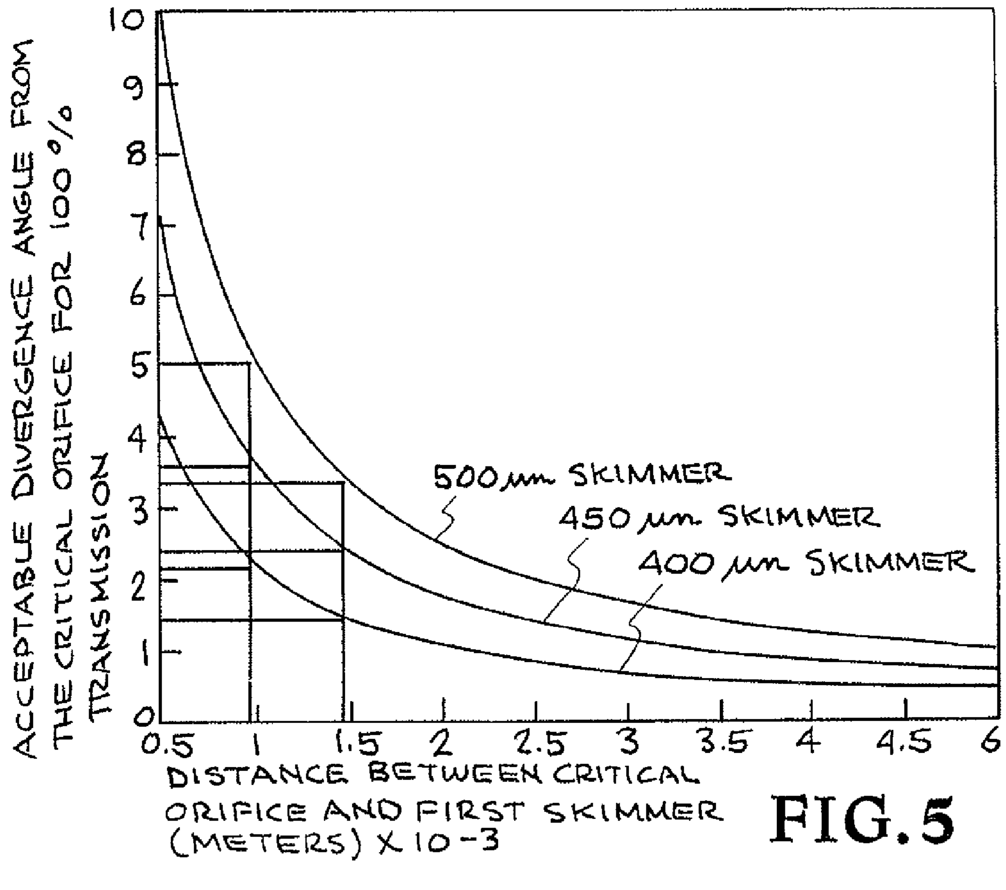
FIG. 5 is a graph showing particle transmission versus skimmer size and distance from inlet nozzle.
Figure 6:
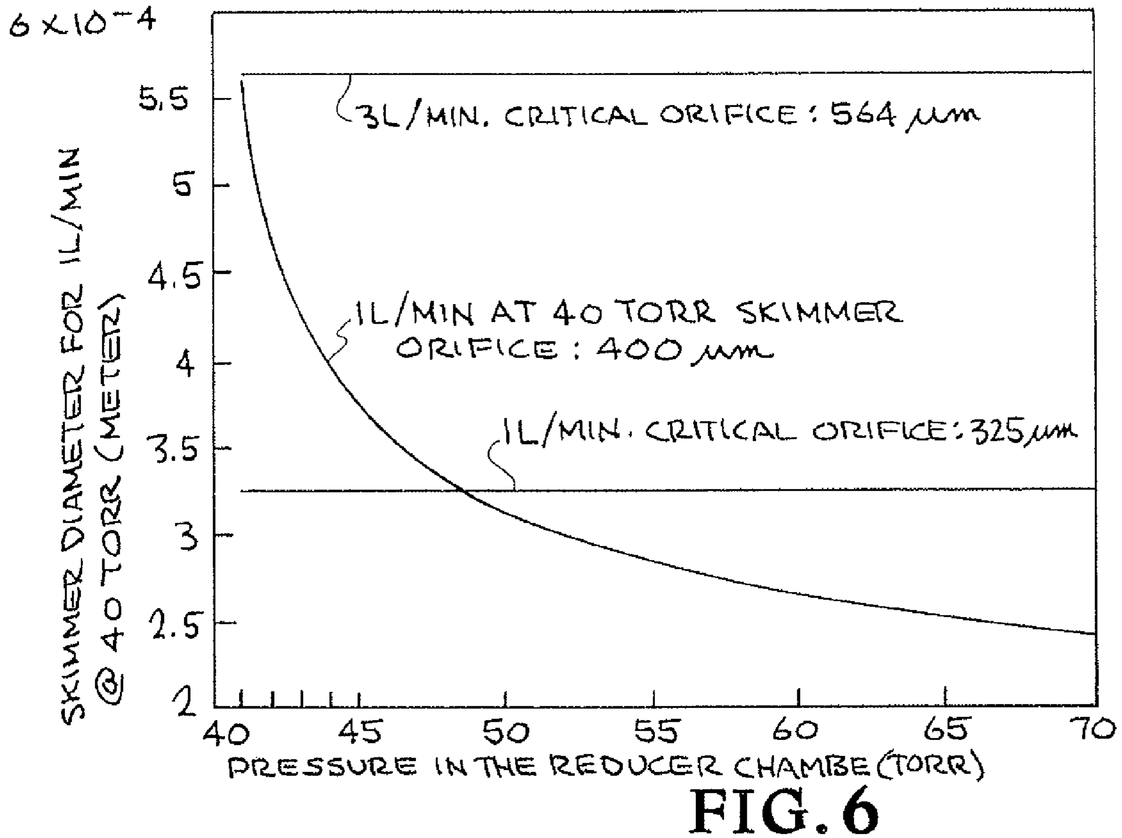
FIG. 6 is a graph showing skimmer diameter for various pressures in the reduction chamber.

The skimmer 206 has a skimmer orifice that is aligned with and spaced downstream from the inlet nozzle 201. The spacing between the skimmer 206 and inlet nozzle 201 forms a gap therebetween which provides fluidic communication between the pumping ports and the inlet nozzle. The skimmer preferably has a conical shape as shown in FIG. 1 for a more efficient pumping but is not limited to this shape. FIG. 5 shows the maximum particle divergence angle that can be handled coming from the inlet nozzle for 100% particle transmission efficiency for various skimmer sizes and distances. The size and distance can be chosen to provide the desired pressure and maximize the particle transmission. Generally, a larger skimmer closer to the nozzle is preferable. While those two parameters will ultimately be determined experimentally but first approximations for the skimmer size and distance from the nozzle can be found using basic fluid dynamic equations as shown in FIG. 6. Generally, the process required to design this PFR component in conjunction with a focusing lens stack completed with an exit nozzle is based on estimations of the Mach number in supersonic expansions, as will be discussed below. In practice, the pressure in the reduction chamber will be measured much lower than expected due to the supersonic expansion. The reduction chamber's purpose is to set the pressure seen by the aerosol focusing device, regardless of the aerosol sampling pressure and flow rate. It provides the decoupling needed to interface the aerosol sampling with the aerosol focusing device.

Figure 7:
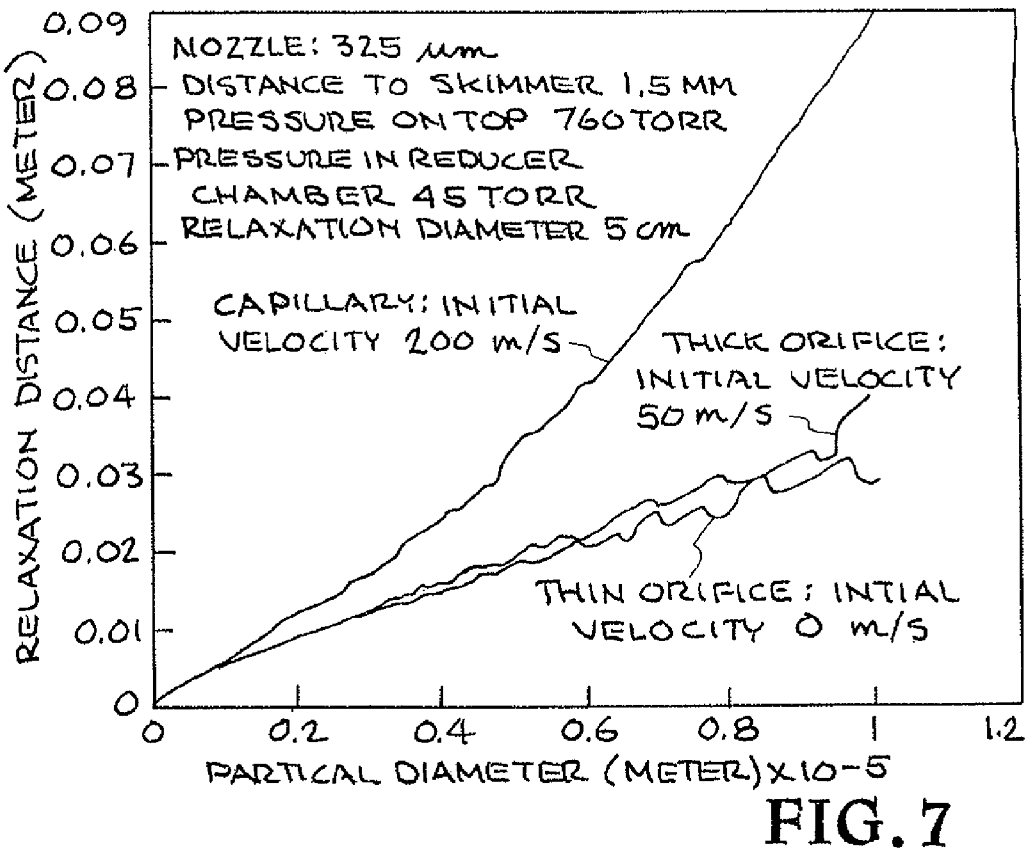
FIG. 7 is a graph showing relaxation chamber dimensions for various inlet nozzles.

The third stage of the PFR is a relaxation chamber 207, whose role is to slow the particles down after they pass the previously described skimmer 206. This step is critical for proper operation of many aerosol focusing devices such as aerodynamic lens stacks. Particles entering the relaxation chamber can have high speeds well above 500 m/s. The stopping or relaxation distance needed will depend on the acceleration particles experience through the supersonic expansion of the nozzle through the skimmer and the pressure and flow inside this chamber. As shown in FIGS. 1 and 2, the relaxation chamber 207 has an outlet 208 which is directly attached to the aerosol focusing device. And FIG. 7 shows relaxation distances for various inlet nozzles that could be used for the first stage.

In order to shorten the computational fluid dynamic (CFD) [2] simulation time and start with a first design, general fluid dynamic equations can be used in a first approximation. Generally, this includes computing the diameter of the sampling nozzle based on the desired sampling flow rate; designing the skimmer diameter and distance from the sampling nozzle to reach the appropriate operating pressure and flow through the relaxation chamber, designing the relaxation chamber based on the estimation of the particle speeds as they pass through the nozzle.

Computing the diameter of the sampling nozzle based on the desired sampling flow rate is accomplished using the following Equation 1 of the system of equations also known as the Prandtl derivation and which is based on the estimation of a pressure drop through a circular orifice for a given flow:

$$Q = \text{Area}\cdot\sqrt{\frac{R_0 T_{top}}{M}}\cdot\sqrt{\gamma\left(\frac{2}{\gamma+1}\right)^{\frac{\gamma+1}{\gamma-1}}} \quad \text{(Equation 1)}$$

where Q is the volumetric flow rate and is constant, Area is the area of the orifice, γ is the heat ratio (e.g. 1.4 for air), R is the gas constant (e.g. ~8.314 for air), $T_{top}$ is the temperature on the top of the orificem, and M is the molecular mass of the gas (e.g. ~29 g/Mol for air). Equation 1 applies for bottom pressures lower than the critical pressure that would choke the orifice. The critical pressure ratio is reached when the gas reaches the speed of sound at the orifice and, for adiabatic and frictionless gas, it can be expressed as follows:

$$\frac{P_{bottom}^{critical}}{P_{top}} = \left(\frac{2}{\gamma+1}\right)^{\frac{\gamma}{\gamma-1}} \quad \text{(Equation 2)}$$

The skimmer diameter and distance from the sampling nozzle is designed to reach the appropriate operating pressure and flow through the relaxation chamber. The critical parameter for this design step lies in estimating the pressure reached in the reduction chamber after the sampling nozzle through pumping. This pressure can be estimated using the characteristics of the pumping system combined with the flow rate of the sampling nozzle. The computation of the skimmer diameter and distance from nozzle yielding the appropriate pressure and flow in the relaxation chamber makes use of the empirical formula for the centerline Mach number M in an expanding jet given by Ashkenas and Sherman [5];

$$M(z) = 3.65\cdot\left(\frac{z}{d_{nozzle}}-0.40\right)^{\gamma-1} - \frac{\gamma+1}{\gamma-1}\cdot\frac{1}{7.3\cdot\left(\frac{z}{d_{nozzle}}-0.40\right)^{\gamma-1}} + \frac{0.2}{\left(\frac{z}{d_{nozzle}}-0.40\right)^{3-(\gamma-1)}} \text{ valid for } 1 < \frac{z}{d_{nozzle}} < 0.67\frac{P_{upstream}}{P_{downstream}} \quad \text{(Equation 3)}$$

where z is the distance from the nozzle along the longitudinal axis, $P_{upstream}$ is the sampling pressure, and $P_{downstream}$ is the pressure in the reduction chamber. The upper boundary defines the location of the mach disc and therefore an upper limit for the distance at which the skimmer can be located from the sampling nozzle. The mass flow is then computed going through a skimmer of a given diameter $d_{skimmer}$ located at a distance $z_{skimmer}$ from the nozzle. Assuming isentropic expansion in the jet, it is possible to express the temperature, Pressure and density of the gas as a function of the Mach number and therefore the distance from the nozzle, as follows:

$$\begin{cases} T(z) = \dfrac{T_{upstream}}{1+\dfrac{\gamma-1}{2}M^2(z)} \\ P(z) = P_{upstream}\cdot\left(1+\dfrac{\gamma-1}{2}M^2(z)\right)^{\frac{-\gamma}{\gamma-1}} \\ \rho(z) = \rho_{upstream}\cdot\left(1+\dfrac{\gamma-1}{2}M^2(z)\right)^{\frac{-\gamma}{\gamma-1}} \end{cases} \quad \text{(Equation 4)}$$

The speed of sound can then be computed as a function of temperature and therefore the gas velocity as a function of distance using the following equation:

$$V_{sound}(z) = \sqrt{\frac{\gamma RT(z)}{M(z)}} \qquad V_{gas}(z) = V_{sound}(z)\cdot M(z) \quad \text{(Equation 5)}$$

The mass flow rate $Q_m$ going through the skimmer can then be written as follows:

$$Q_m(z_{skimmer}) = \rho(z_{skimmer})\cdot\pi\left(\frac{d_{skimmer}}{2}\right)^2\cdot V_{gas}(z_{skimmer}) \quad \text{(Equation 6)}$$

Since the lens stack was designed for a given flow rate equivalent at atmosphere pressure, the mass flow required through the skimmer to yield the proper operating condition is given as follows:

$$Q_m(z_{skimmer}) = \rho_{atmosphere}\cdot\frac{Q_{equ}(L/\text{min})}{1000.60} \quad \text{(Equation 7)}$$

Figure 8:
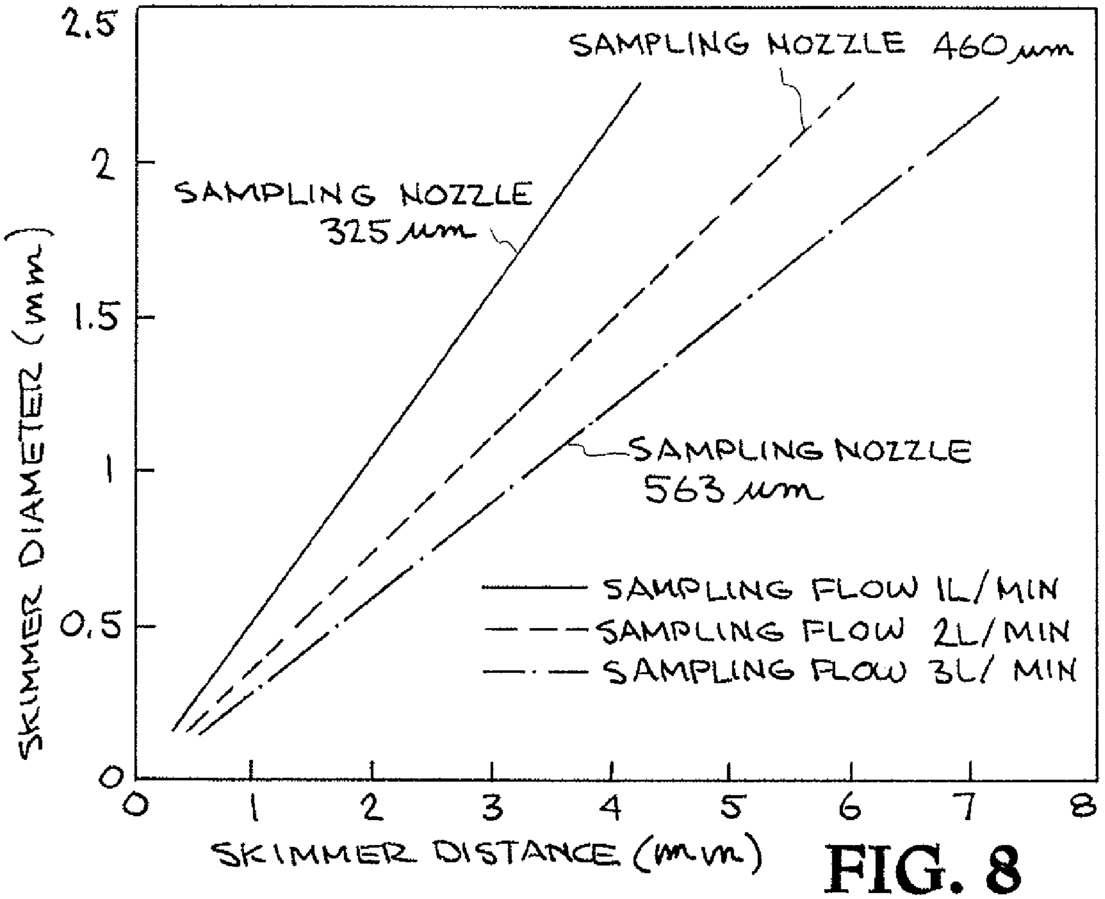
FIG. 8 is a graph showing PFR skimmer design for an interface to a 20 Torr, 1 L/min equivalent flow at one atmosphere (or 3.8 L/min flow at 20 Torr).

Using Equations 6 and 7, the skimmer distance can be expressed as a function of the skimmer diameter yielding the proper operating condition for the lens stack. FIG. 8 shows an example for a PFR interfacing to a lens stack operating at 20 Torr and 0.1 L/min equivalent flow rate at one atmosphere (or 3.8 L/min at 20 Torr). It is notable that the skimmer diameter should be chosen so that it is larger than the sampling nozzle in order to optimize the transmission efficiency of aerosol particles to the relaxation chamber.

And finally, the design of the relaxation chamber is based on the estimation of the particle speeds as they pass through the nozzle. The equation of motion for a particle in a fluid using the drag force [6] is given by Equation 8.

$$\frac{dV_{particle}}{dt} = \frac{(V_{fluid}-V_{particle})}{\underbrace{\dfrac{\rho_{particle}d^2_{particle}}{18\mu}\left(1+1.66\dfrac{2}{d_{particle}}\left[\dfrac{\lambda_{standard}}{\left(\frac{760}{P}\right)\left(\frac{T}{298}\right)\left(\frac{1+110/298}{1+110/T}\right)}\right]\right)}_{\text{Cunningham correction factor } C_c}} \quad \text{(Equation 8)}$$

$$\frac{dV_{particle}}{dt} = \frac{(V_{fluid}-V_{particle})}{\tau}$$

where τ is the particle relaxation time in the fluid corrected by the Cunningham factor Cc. We must note that the corrected relaxation time is dependent on the gas temperature T and pressure P. Equation 4 must then be used to estimate those parameters as the particle travels through the supersonic expansion. In order to estimate the speed of the fluid at all time from the tip of the nozzle, Equation 5 is used with an extended version of Equation 3 for the expression of the Mach number by using a polynomial fit giving Mach 1 at the tip of the nozzle. However, the validity of Equation 3 has to be reduced to start at $$2 < \frac{z}{d_{nozzle}}$$

for a smoother extension. Equation 3b below shows the extension of the Mach number estimation for air.

$$M(z) = 1+1.6515\cdot\frac{z}{d_{nozzle}} 0.1164\cdot\left(\frac{z}{d_{nozzle}}\right)^2 \text{ for } 0 < \frac{z}{d_{nozzle}} < 2 \quad \text{(Equation 3b)}$$

Figure 9:
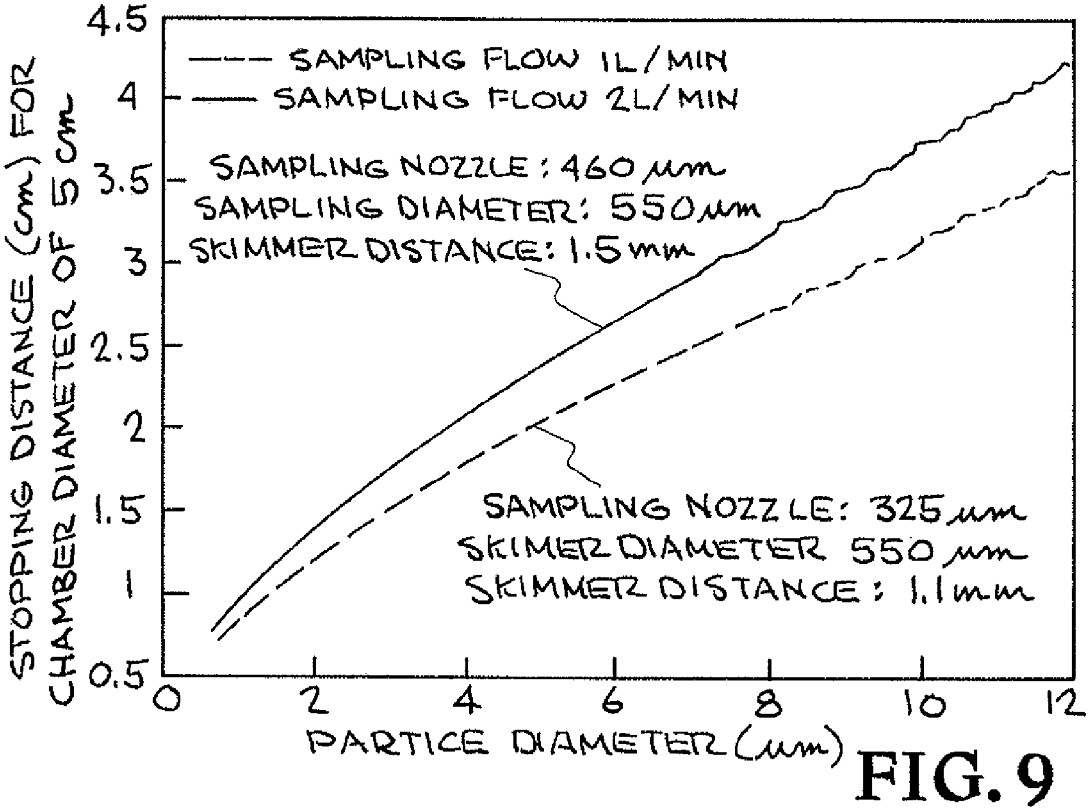
FIG. 9 is a graph showing various relaxation distance designs for an interface to a 20 Torr, 1 L/min equivalent flow at one atmosphere (or 3.8 L/min flow at 20 Torr) lens stack. Relaxation chamber diameter of 5 cm

The numerical integration of Equation 8 is then performed, yielding the speed of the particles when they pass through the skimmer. The stopping distance is then estimated when particles reach 90% of the gas speed within the relaxation chamber. The gas speed in the relaxation chamber is given using the volumetric flow rate and the diameter of the relaxation chamber. This diameter should be large enough to accommodate for eventual particle divergence and yield a very low gas speed. FIG. 9 shows some stopping distances estimated for two different PFR configurations.

C. Aerodynamic Focusing Lens Stack

The second component of the AFS is the aerodynamic focusing lens stack. As can be seen in FIG. 3, the lens stack type of aerosol focusing device 102 is based on stacked orifices, shown as stacked lens modules 302, that contract the flow lines as gas is passed through. Particles following the stream lines will be focused toward the centerline due to their inertia. At a downstream end of the lens stack is an exit nozzle 303 through which particles exit the AFS of the present invention. In FIG. 3 the stack of lens modules 302 and the exit nozzle 303 are shown vertically aligned by a barrel 301.

As previously mentioned, in order to shorten the computational fluid dynamic (CFD) [2] simulation time and start with a first design, general fluid dynamic equations can be used in a first approximation. The present invention provides an automated design algorithm for sizing the various lens diameter to produce a focusing device for a given particle size range and operating conditions, so that various interface systems could be designed rapidly for different operating conditions without the need of lengthy computational fluid dynamic and costly bench top experimentation. Using basic analytical fluid dynamic equations based on the Stokes number and the Prandtl formula for describing the pressure drop through an orifice, the present invention estimates the number and dimensions of lenses required to create a focused particle beam for any particle size range.

In order to produce a preliminary design of a lens stack for a given particle size range, the following assumption were made on the type of flow that will be present within the lens stack. The first assumption is that the flow will be laminar and therefore, particles in this type of flow will behave according to the Stokes number formula. This implies in particular that the Reynolds numbers for the various lenses in operating conditions (pressure and flow rate) are below 200. The second assumption is that the gas behavior when going through a lens can be modeled as an adiabatic expansion. This assumes that there is no temperature loss or gain during the expansion. This is true if the expansion is fast and therefore if the lens thickness is negligible. The third assumption is that the gas stays at temperature constant equal to the outside temperature between the lenses, which is a reasonable assumption if the actual device is manufactured out of metal. It must be noted that the design procedure can be easily modified for an isentropic flow where the temperature of the gas has to be tracked within the various region of the device.

The first main equation that is used in this design method is based on the estimation of a pressure drop through a circular orifice for a given flow. Using the previous assumptions, we can derive the value of the volumetric flow rate for a circular orifice in an adiabatic, frictionless expansion. The following formula is obtained:

$$Q = \text{Area}\cdot\left(\frac{P_{bottom}}{P_{top}}\right)^{\frac{1}{\gamma}}\cdot\left\{\frac{2\gamma}{\gamma-1}\cdot\frac{R_0 T_{top}}{M}\left[1-\left(\frac{P_{bottom}}{P_{top}}\right)^{\frac{\gamma-1}{\gamma}}\right]\right\}^{\frac{1}{2}} \quad \text{(Equation 9)}$$

where Q is the volumetric flow rate, Area is the area of the orifice, γ is the heat ratio (1.4 for air), R is the gas constant (~8.314 for air), $T_{top}$ is the temperature on the top of the orifice and M is the molecular mass of the gas (~29 g/Mol for air). This relation is true as long as the pressure on the bottom is not lower than the critical pressure that would choke the orifice. As previously discussed, the critical pressure ratio is reached when the gas reaches the speed of sound at the orifice and, for adiabatic and frictionless gas, it can be expressed by Equation 2 restated here as:

$$\frac{P_{bottom}^{critical}}{P_{top}} = \left(\frac{2}{\gamma+1}\right)^{\frac{\gamma}{\gamma-1}} \quad \text{(Equation 2)}$$

Also as previously discussed, for bottom pressures lower than the critical pressure, the volumetric flow rate is constant as described by Equation 1, restated here as:

$$Q = \text{Area}\cdot\sqrt{\frac{R_0 T_{top}}{M}}\sqrt{\gamma\left(\frac{2}{\gamma+1}\right)^{\frac{\gamma+1}{\gamma-1}}} \quad \text{(Equation 1)}$$

This system of equations is known as the Prandtl derivation.

The second main equation is based on the rewriting of the Stokes number equation for a given particle going through an orifice operating at a given flow, and expressed in Equation 10:

$$st = \underbrace{\left(1+1.66\frac{2}{d_{particle}}\left[\lambda_{standard}\left(\frac{760}{P}\right)\left(\frac{T}{298}\right)\left(\frac{1+110/298}{1+110/T}\right)\right]\right)}_{\text{Cunningham correction factor } C_c}\cdot \rho_{particle}\cdot d_{particle}^2\cdot\underbrace{\frac{Q}{\pi\left(\frac{d_{lens}}{2}\right)^2}}_{U_{gas}}\cdot\frac{1}{18\cdot\mu\cdot d_{lens}} \quad \text{(Equation 10)}$$

where $d_{particle}$ is the particle diameter, $\rho_{particle}$ is the particle density, $\lambda_{standard}$ is the standard gas mean free path, P is the gas pressure, T is the gas temperature, μ is the gas dynamic viscosity and $d_{lens}$ is the orifice diameter. This equation can be rewritten in order to express the orifice diameter given a set Stokes number and particle, and is expressed as Equation 11:

$$d_{lens} = \sqrt[3]{\left(1+1.66\frac{2}{d_{particle}}\left[\lambda_{standard}\left(\frac{760}{P}\right)\left(\frac{T}{298}\right)\left(\frac{1+110/298}{1+110/T}\right)\right]\right)\cdot\rho_{particle}\cdot d_{particle}^2\cdot\frac{4\cdot Q}{\pi}\cdot\frac{1}{st\cdot 18\cdot\mu}} \quad \text{(Equation 11)}$$

The third and last equation used in this design algorithm is the Reynolds number formula used to constrain and assess the turbulence of the flow throughout the stack design. This formula is given in Equation 12.

$$Re = \underbrace{\frac{Q}{1000 \cdot 60 \cdot \pi \cdot \left(\frac{d_{lens}}{2}\right)^2}}_{\text{Gas velocity}} \cdot d_{lens} \cdot \underbrace{\frac{\rho}{\mu}}_{\text{Inverse of kinematic viscosity}} \quad \text{(Equation 12)}$$

where ρ is the density of the gas (to adjust with pressure depending of the gas type) and μ is the dynamic viscosity. Depending on the flow type used, flow, temperature and density will have to be adjusted with pressure. For a gas operating at constant temperature, things are simpler and can be summarized as follows:

$$PV = cst \quad \text{(Equation 13)}$$

$$Q_1 = Q_2 \cdot \frac{P_2}{P_1}$$

$$\rho_1 = \rho_2 \cdot \frac{P_1}{P_2}$$

If the gas was considered isentropic throughout the stack, which would simulate a nozzle made out of a low temperature-conductive material, $$\frac{P}{\rho^\gamma} = cst$$

should be considered instead.

The algorithm used for designing a focusing lens stack makes use of a step down approach. It assumes that larger particles will be focused by the first lenses and smaller particles by subsequent lenses. In order to characterize the algorithm, we need to formalize the previous equations. Equations 1, 2, and 9 can be combined into the pressure drop equation that will be written as follows.

$$\text{DROP}(T,Q,P_{top},P_{bottom},d_{orifice},\gamma,R,M)=0 \quad \text{(Equation 14)}$$

Where, T is the temperature of the incoming gas, Q is the volumetric flow rate, $P_{top}$ is the pressure upstream, $P_{bottom}$ is the pressure downstream, $d_{orifice}$ is the diameter of the orifice, γ is the gas heat ratio, R is the gas constant and M is the molecular mass.

Equation 10 can be formalized as follows.

$$\text{FOCUS}(T,Q,P,\lambda,\mu,d_{orifice},d_{particle},\rho_{particle},Stk)=0 \quad \text{(Equation 15)}$$

Where, T is the temperature of the incoming gas, Q is the volumetric flow rate, P is the pressure upstream, λ is the standard mean free path of the gas, μ is the gas viscosity, $d_{orifice}$ is the diameter of the orifice, $d_{particle}$ the diameter of the particle, $\rho_{particle}$ is the density of the particle and Stk is the stoke number.

A preferred embodiment of the algorithm used to automate the design requires initial input parameters whose list is given below:

Particle size range considered (and their density which should be fixed across the design) defined as [$dpart_{min}$, $dpart_{max}$]. The upper range of the first lens will be noted as $d_{part}$[1]=$dpart_{max}$.

Gas characteristics (viscosity, mean free path, heat ratio, Gas constant, Molecular mass, flow type).

Temperature on top of the lens stack defined as T[1].

Pressure on top of the lens stack defined as P[1].

Flow through the lens stack equivalent at atmosphere pressure defined as $Q_{equ}$. The actual flow value at the top pressure is defined as Q[1].

$$Q[1] = Q_{equ}\frac{P_{atm}}{P[1]}$$

for gas flow at temperature constant)

Focusing tightness defined as Stokes number range. A stoke number around 1 yield the best focusing, although it has been shown that optimum stokes numbers vary with Reynold numbers P[3]. The Stokes number range is defined as [$Stk_{min}$, $Stk_{max}$].

The algorithm then iterates, starting with the first lens. For each lens i, the computational steps are as follows:

Using the upstream pressure and flow, define the lens diameter $d_{lens}$[i] that yields the upper Stokes number range for the current maximum particle diameter by solving the following equation for $d_{lens}$[i].

$$\text{FOCUS}(T[i],Q[i],P[i],\lambda,\mu,d_{lens}[i],d_{particle}[i],\rho_{particle},Stk_{max})=0$$

Compute the particle maximum diameter that will be focused by the next lens by solving the following equation for $d_{part}$[i+1] using the previously computed lens diameter.

$$\text{FOCUS}(T[i],Q[i],P[i],\lambda,\mu,d_{lens}[i],d_{particle}[i+1],\rho_{particle},Stk_{min})=0$$

Compute the pressure drop across the previously computed lens by solving the following equation for P[i+1].

$$\text{DROP}(T[i],Q[i],P[i],P[i+1],d_{lens}[i],\gamma,R,M)=0$$

Update the flow Q[i+1] and temperature T[i+1] for the previously computed pressure Q[i+1] depending on the type of flow. For a gas at temperature constant, $$T[i+1] = T[i] \text{ and } Q[i+1] = Q[i]\frac{P[i]}{P[i+1]} = Q_{equ}\frac{P_{atm}}{P[i+1]}$$

The iteration stops when the next maximum particle diameter $d_{particle}$[i+1] is smaller than $dpart_{min}$. The last step of the algorithm is a validation steps involving the computation of the Reynolds number for each lens using Equation 12. The number must stay low in order to guarantee that the flow will stay laminar and that a stokes number of 1 will yield the best focusing.

Figure 10:
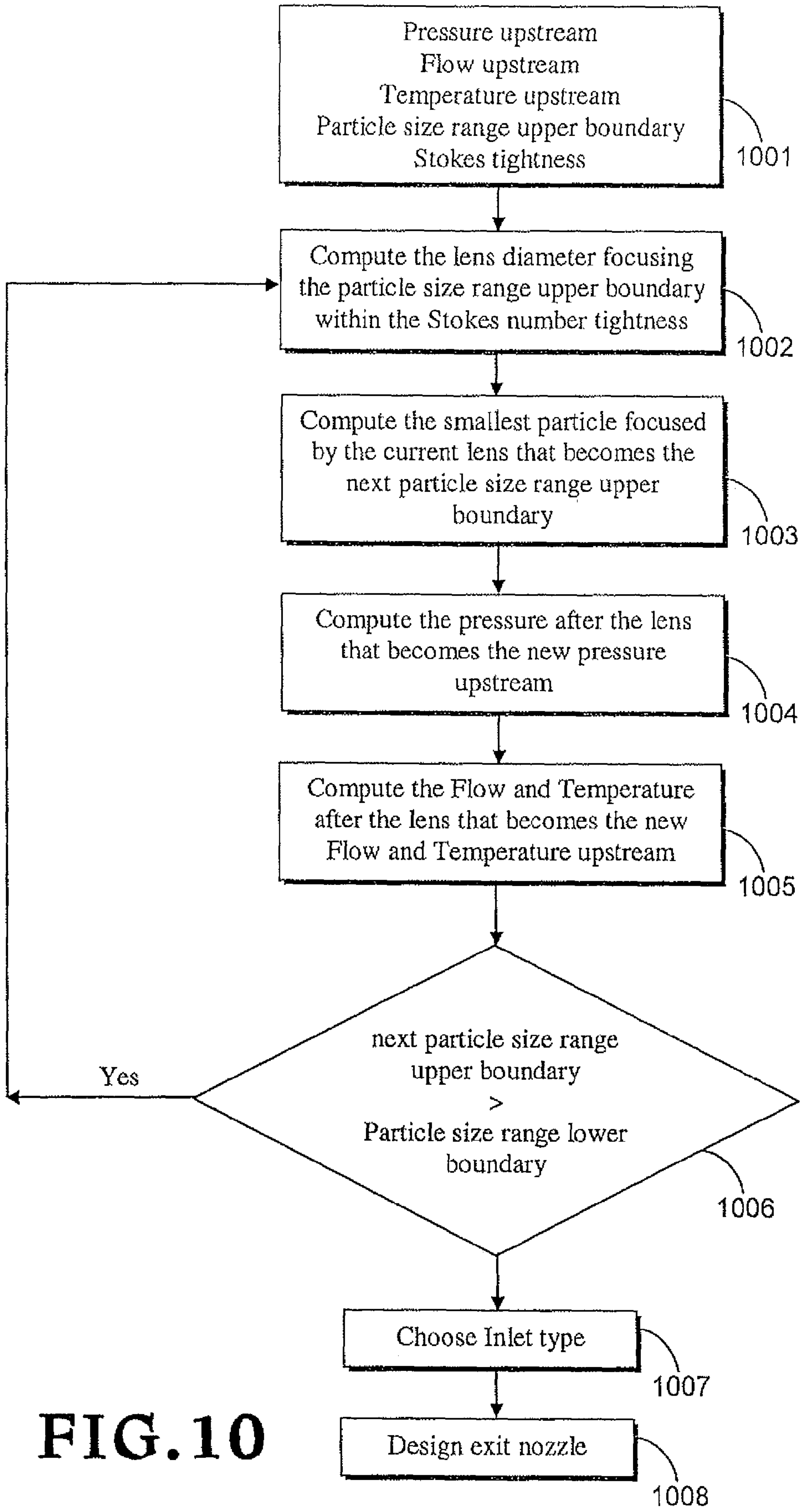
FIG. 10 is a flow chart

FIG. 10 shows an exemplary embodiment of the process described above for designing a focusing lens stack. First at block 1001, input parameters are received, including pressure upstream, flow upstream, temperature upstream, particle size range upper boundary, Stokes tightness. Then at block 1002, a computation is performed for the lens diameter focusing the particle size range upper boundary within the Stokes number tightness. Then at block 1003, computation is performed for the smallest particle focused by the current lens that becomes the next particle size range upper boundary. At block 1004, a computer is performed for the pressure after the lens that becomes the new pressure upstream. At block 1005, a computer is performed for the flow and temperature after the lens that becomes the new flow and temperature upstream. Then at block 1006 a determination is made whether the next particle size range upper boundary is greater than the particle size range lower boundary. If yes, control is passed back to block 1002. If not, then the algorithm proceeds to block 1007 where the inlet type is chosen. And at block 1008, the exit nozzle is designed, as will be discussed below.

Figure 11:
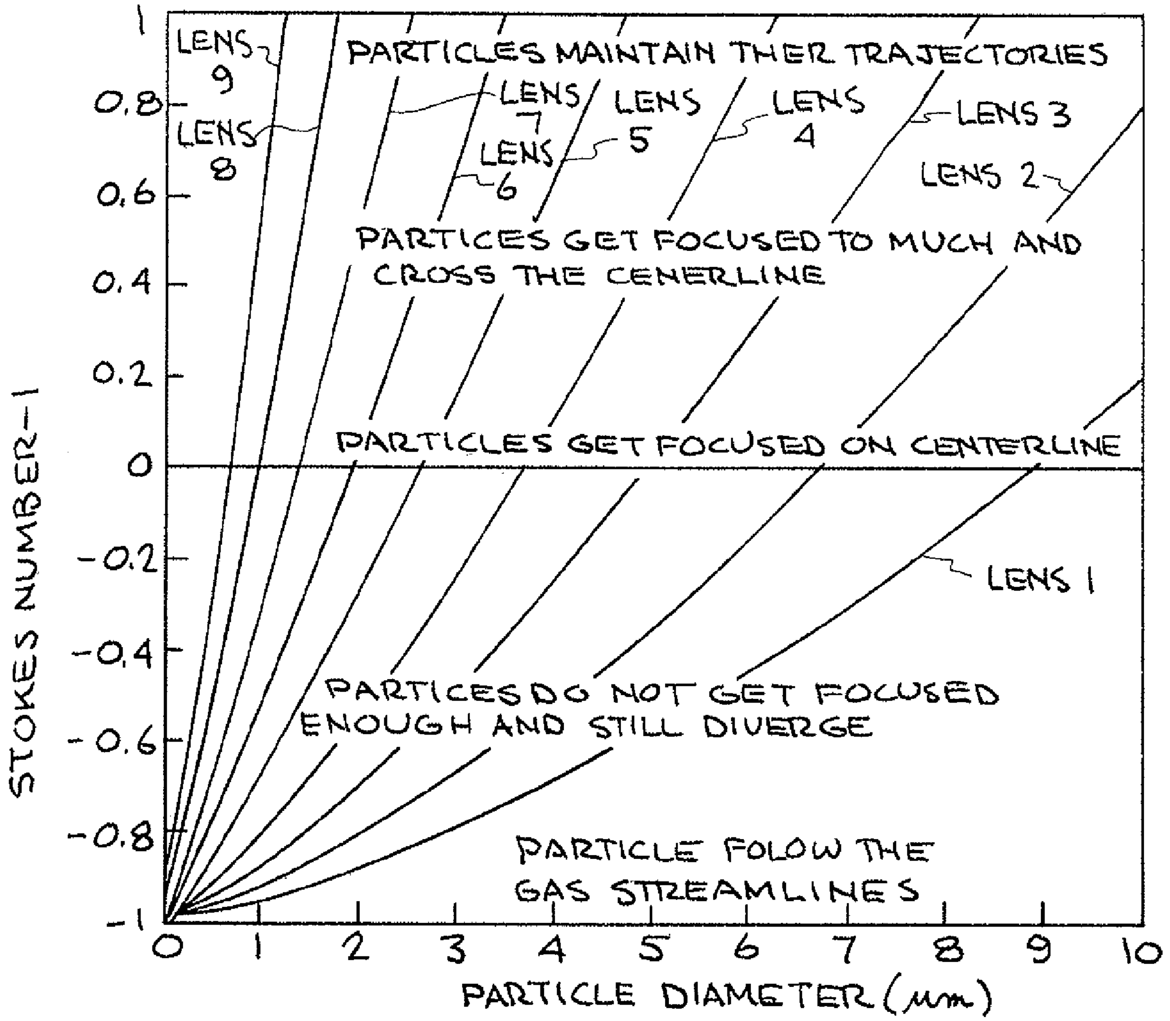
FIG. 11 is a graph showing an exemplary step down lens stack design focusing a particle size range of [0.7 μm, 10 μm].

FIG. 11 describes an illustrative lens stack design for air at 298K operating at 20 Torr for an equivalent flow rate of 0.1 L/min at 760 Torr, a Stokes range of [0.8, 1.2] and a particle diameter range of [0.7 μm, 10 μm]. For this particular design, nine lens were required. The following Table 1 shows the actual lens design of FIG. 11 with the corresponding Reynolds number and focused particle size.

TABLE 1

Design values for a 20 Torr design at 0.1 L/min flow equivalent at 760 Torr

| Lens Number | Lens Diameter (mm) | Particle size range (μm) | Reynolds Number |
|---|---|---|---|
| 1 | 3.36 | [7.65, 10.0] | 42.06 |
| 2 | 2.94 | [5.78, 7.65] | 48.14 |
| 3 | 2.57 | [4.31, 5.78] | 55.09 |
| 4 | 2.24 | [3.16, 4.31] | 63.03 |
| 5 | 1.96 | [2.28, 3.16] | 72.09 |
| 6 | 1.72 | [1.63, 2.28] | 82.40 |
| 7 | 1.50 | [1.14, 1.63] | 94.06 |
| 8 | 1.32 | [0.79, 1.14] | 107.15 |
| 9 | 1.16 | [0.54, 0.79] | 121.61 |

D. Exit Nozzle Design

Figure 12:
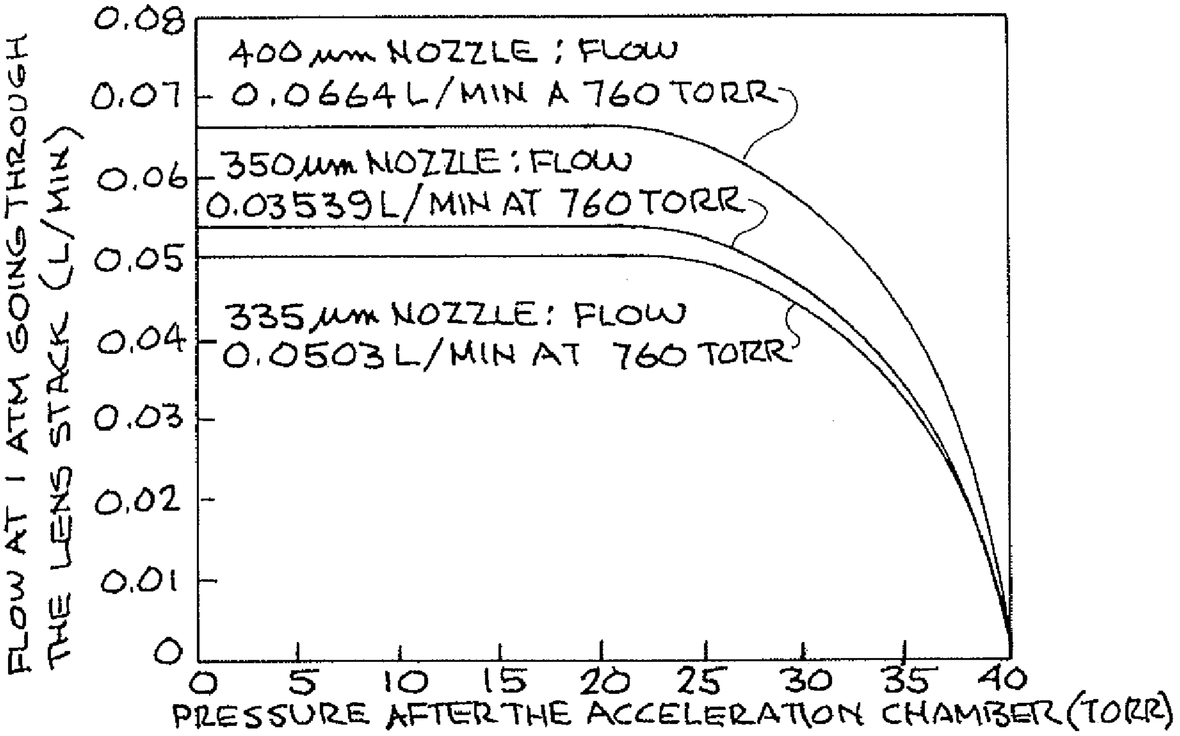
FIG. 12 is a graph illustrating the effect of the exit nozzle on the overall flow going through the focusing lens stack.

In order to guarantee that the required flow rate is met for an aerosol focusing device such as an aerodynamic focusing lens stack, the aerosol focusing device exit nozzle must be designed accordingly. The exit nozzle that has two main purposes. The first is to lock the flow and pressure observed in the relaxation chamber after the PFR skimmer. The second is to accelerate particles into vacuum so that particle sizing from their aerodynamic diameter can be eventually done. This is achieved by designing a nozzle that operates in a chocked mode, thus locking the flow and accelerating particle through supersonic expansion so as to decouple flow from pressure. Its dimensions will depend on the fact that the pressure on top of the stack will be maintained at a fixed operating value. FIG. 12 shows how the exit nozzle can affect the flow rate going through the aerosol focusing device chosen here as a custom focusing lens stack.

The design of the nozzle diameter is entirely defined by the design parameters of the lens stack. The pressure after the last lens is estimated iteratively as done during the lens stack design algorithm. The volumetric flow that is required through the exit nozzle can then be estimated using Equation 13 for the pressure after the last lens. Equation 1 is then used to define the exit nozzle diameter operating in chocked mode. Table 2 summarizes the various design parameters necessary to interface to the lens stack described in Table 1 when the sampling flow is set at around 1 L/min.

TABLE 2

PFR and exit nozzle for a lens stack operating at 20 Torr at 0.1 L/min flow equivalent at 760 Torr

| Parameter | Dimensions |
|---|---|
| PFR sampling nozzle diameter | 340 μm |
| PFR skimmer diameter | 550 μm |
| PFR skimmer distance | 1147 μm |
| Exit Nozzle | 651 μm |

Figure 13:
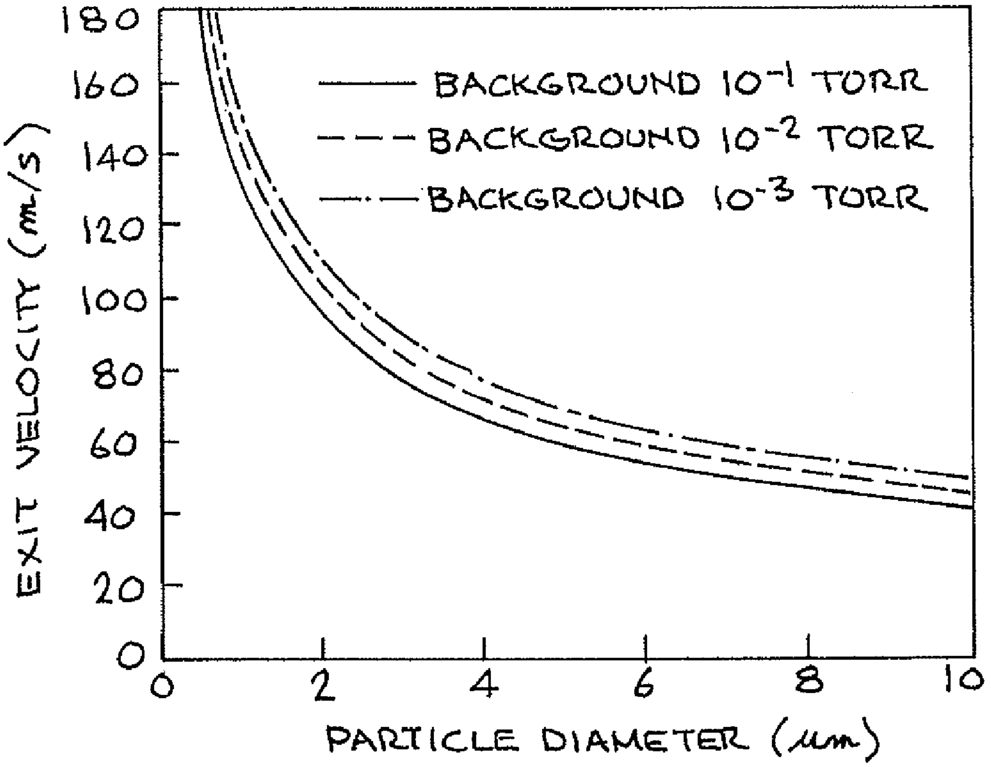
FIG. 13 is a graph illustrating the effect of background pressure after the exit nozzle on exit velocities.

The exit velocities are estimated using Equation 8 and the extended Mach number equation. In this computation, we assume that the particle will reach their maximum velocities once they reach the Mach disc when the gas is compressed back to the background pressure. The back ground pressure has to ensure that the exit nozzle operates in chocked mode. However, once it meets this requirement, the background pressure after the exit nozzle will define the exit velocity range of the particles. FIG. 13 shows the various exit velocities that should be expected for various background pressure after the nozzle.

E. Orifice Sizing Predictive Effect on the Focusing Size Range

Experiments performed at the Lawrence Livermore National Laboratory have shown that the dimensions of the PFR and exit nozzle have a far more critical effect on the focusing device than the precise diameter dimensions of the actual lenses as they mainly control the flow and pressure through the stack and therefore affect the particle range being focused. As a rule of thumb, based on the Stokes number (Equation 10), reducing the flow through the lens stack will shift the range of focused particle towards larger particles, and increasing the flow will shift the range towards smaller particles. In terms of pressure, a decrease of pressure in the relaxation chamber will shift the range of focused particle towards smaller particles, and increasing the relaxation pressure will shift the range towards larger particles. Equation 1 used to design the exit nozzle describes how it will define the flow going through the lens stack and especially how a larger nozzle will yield a larger flow and thus focus smaller particles. The pressure-flow reducer is also an important player on how the operating conditions of the lens stack are set and in particular on the pressure value in the relaxation chamber. It is mainly based on how much mass flow is going through the skimmer. More mass flow will have the tendency to increase the pressure in the relaxation chamber as the exit nozzle is limiting the outgoing flow. A larger skimmer will yield a larger mass flow, increasing the pressure and thus shifting the range toward larger particles. The distance of the PFR skimmer to the sampling nozzle will reduce the mass flow as the gas density goes down, thus decreasing the relaxation chamber pressure and shifting the focusing range toward smaller particles. FIG. 13 shows the quantitative effect on those dimensions when they are varied around the optimum designed values. It must be noted that the exit nozzle has the most important effect. In addition, the PFR design has one free parameter, and therefore, if the distance to the sampling nozzle can be experimentally adjusted, it is possible to compensate for skimmer diameter machining errors.

G. CFD Validation and Experimental Results

In order to first assess and validate the analytical estimation of the design, Computational Fluid Dynamic (CFD) simulations have been run using the two dimensional, axis symmetric, high Mach number, compressible flow solver STAR-CCM+™ from CTD-Adapco. In addition, two devices have been built in stainless steel and brass and tested at Lawrence Livermore National Laboratory, and experimental measurements taken for a focusing device designed to sample at 1 L/min at atmospheric pressure and focus particles between 1 μm to 10 μm diameter into vacuum. The experimental results were then compared with analytical prediction and computational fluid dynamic and show that there is a very good agreement between theory and experiment. Generally, it has been shown that replacing conventional critical orifice sampling interface with out Pressure-Flow reducer can greatly improve the sampling rate and efficiency of focusing devices based on aerodynamic lens stacks, thus increasing the sensitivity of aerosol analysis instrumentation. Actual device behaviors seem to be following closely numerical predictions from the design tool for the pressure-flow reducer skimmer adjustment, the lens stack focusing range and the exit nozzle particle exit velocities.

G.1 Mechanical Design and Experimental Setup

A device including a pressure flow reducer as described in Table 2, a 9 lens focusing stack as described in Table 1 and an exit nozzle has been built. FIG. 2 shows the mechanical design for both the pressure flow reducer and the lens stack. The pressure flow reducer has been designed so that the skimmer distance to the sampling nozzle can be adjusted using shims of variable thickness. The lens stack is designed around stackable lens modules. A module consists of a lens and a 1.5 cm tall spacer. Each module is sealed from the next using an O-ring. The nine modules forming the focusing stack are then inserted in a barrel connected at one end to the pressure flow reducer and at the other end to a nozzle. A first device was built made out of stainless steel. However, machining revealed to be more complex than expected for centering the orifices and maintaining good alignment between the various lens modules once assembled. A second device was then made out of brass allowing a more precise centering of the various orifices.

G.2 Pressure Adjustment in the Pressure-Flow Reducer

Figure 14A:
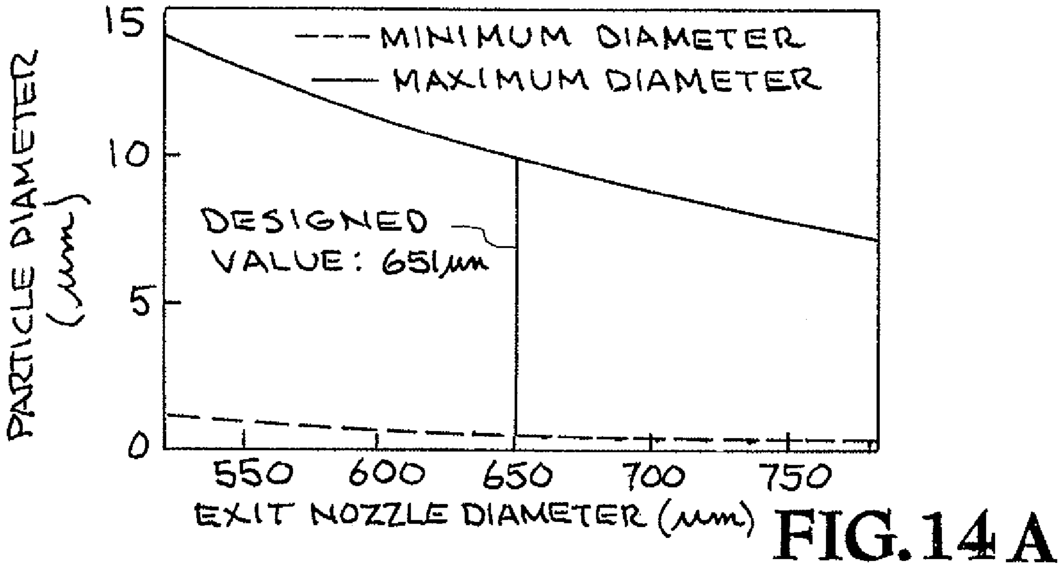
FIG. 14 is a graph illustrating the effect of dimensions on the focusing range for the lens stack described in Table 1.
Figure 14B:
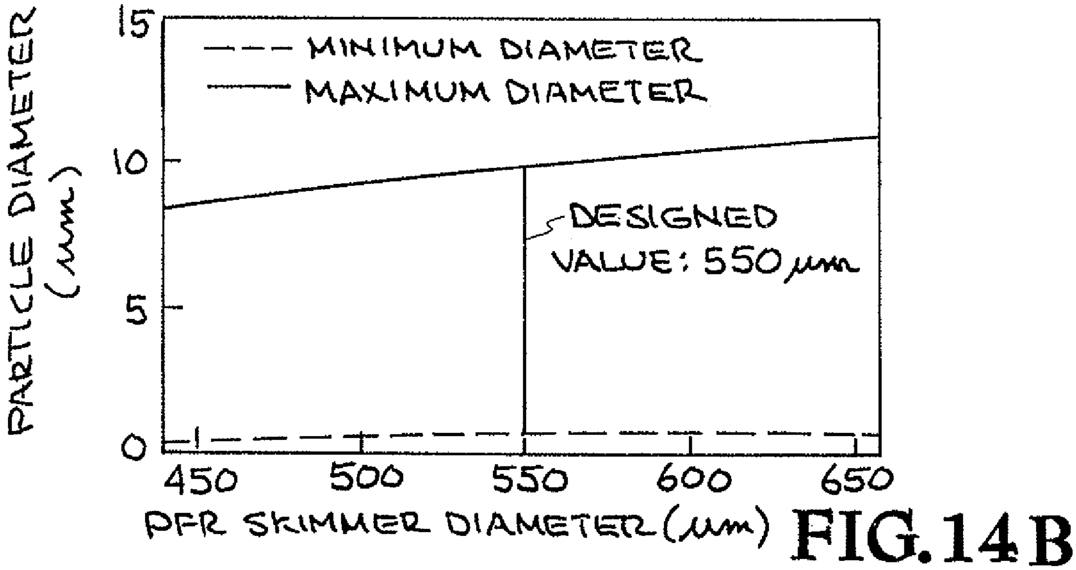
Figure 14C:
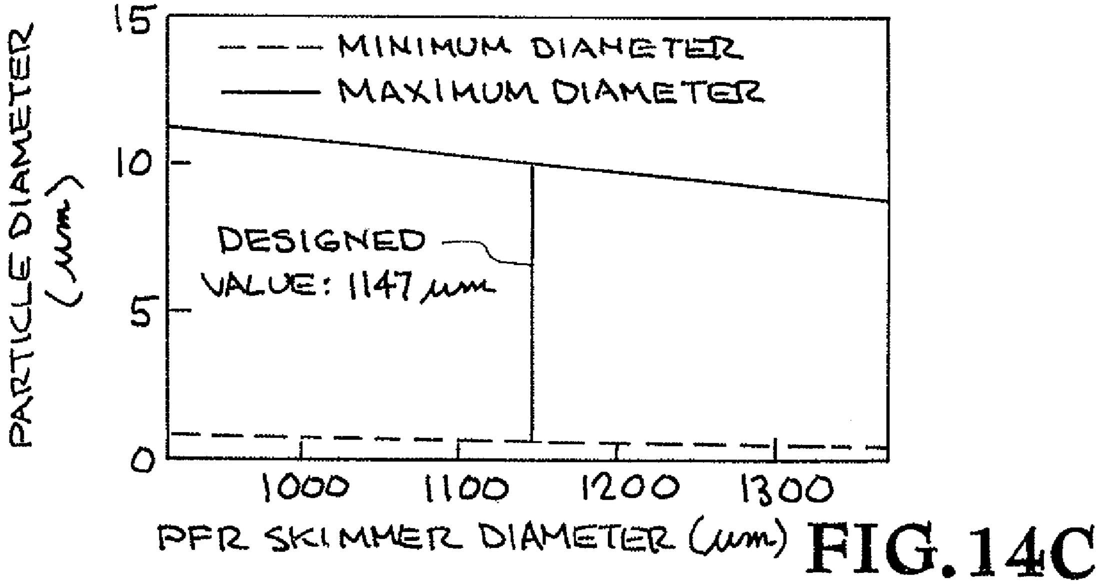
Figure 15:
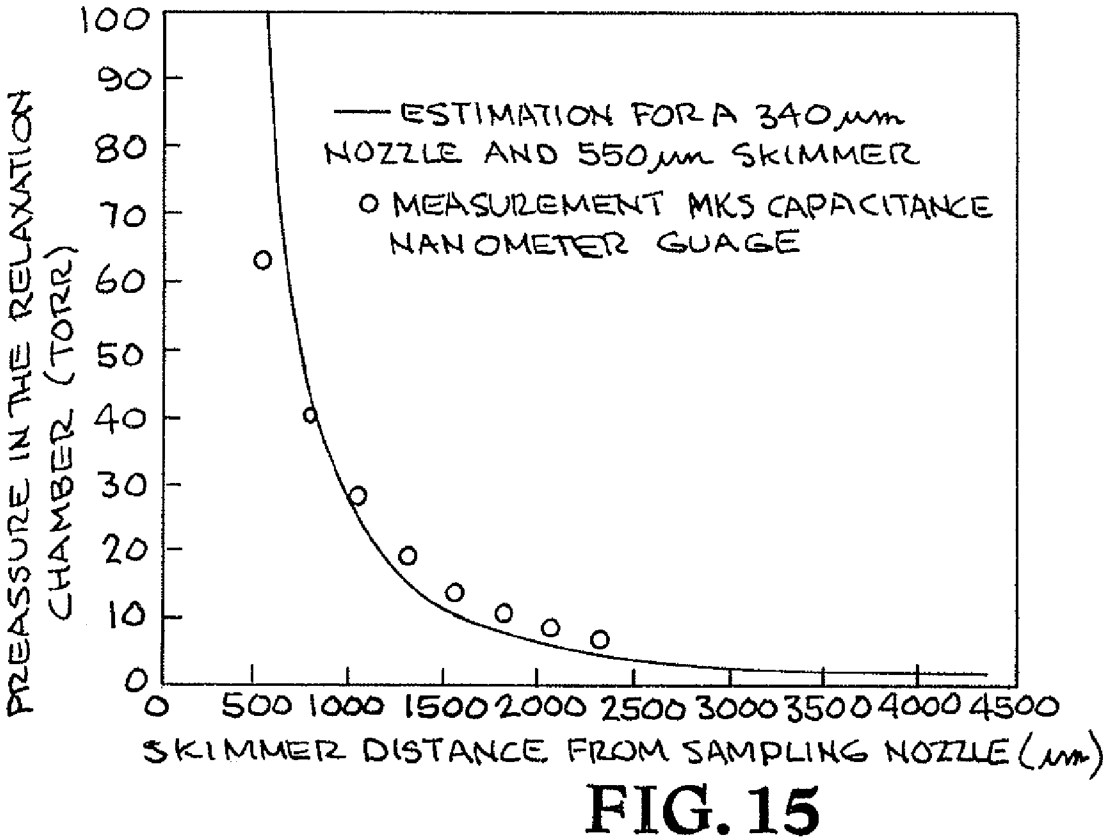
FIG. 15 is a graph showing PFR skimmer distance relation with pressure in the relaxation chamber for a 650 um exit nozzle.

From the theoretical section, it can be expected that if the exit nozzle is designed properly, reaching an operating pressure of 20 Torr in the relaxation chamber will yield the proper flow and therefore operating conditions. The design tool for the pressure flow reducer gives an approximation of the distance between sampling nozzle and skimmer for proper operation. This is due to the fact that the estimation is performed using flow properties found in the centerline. However, because the skimmer diameter is designed to be larger than the sampling nozzle, we allowed room for experimental optimization from the designed values and eventual machining error on the skimmer diameter dimensions. In addition, pressure values obtained for different distances allow us to validate our analytical model as it is defined by the estimation of the pressure drop at each and every lens within the stack. Finally, being able to slightly change the distance and therefore the pressure, allows the particle size range being focused to be slightly adjusted if required as FIG. 14 shows. Pumping for the Pressure flow reducer is done from both side using a rough pump V500. Some measurements were taken using an MKS 626A Baratron capacitance manometer with the MKS PDR2000 gauge controller for various skimmer distances. The PFR was setup with a 340 μm sampling nozzle and a 550 μm skimmer. The exit nozzle of the lens stack as described in Table 1 was set to 650 μm. FIG. 15 shows the measurement compared with pressure estimation using the derivation described in the theoretical section. The gauge was calibrated by setting the zero for a pressure of $10^{-4}$ Torr as recommended by the vendor. A very good match can be seen, even though slight adjustment had to be made from the designed value in order to reach the 20 Torr.

G.3 Exit Velocities and Modeling

Figure 16:
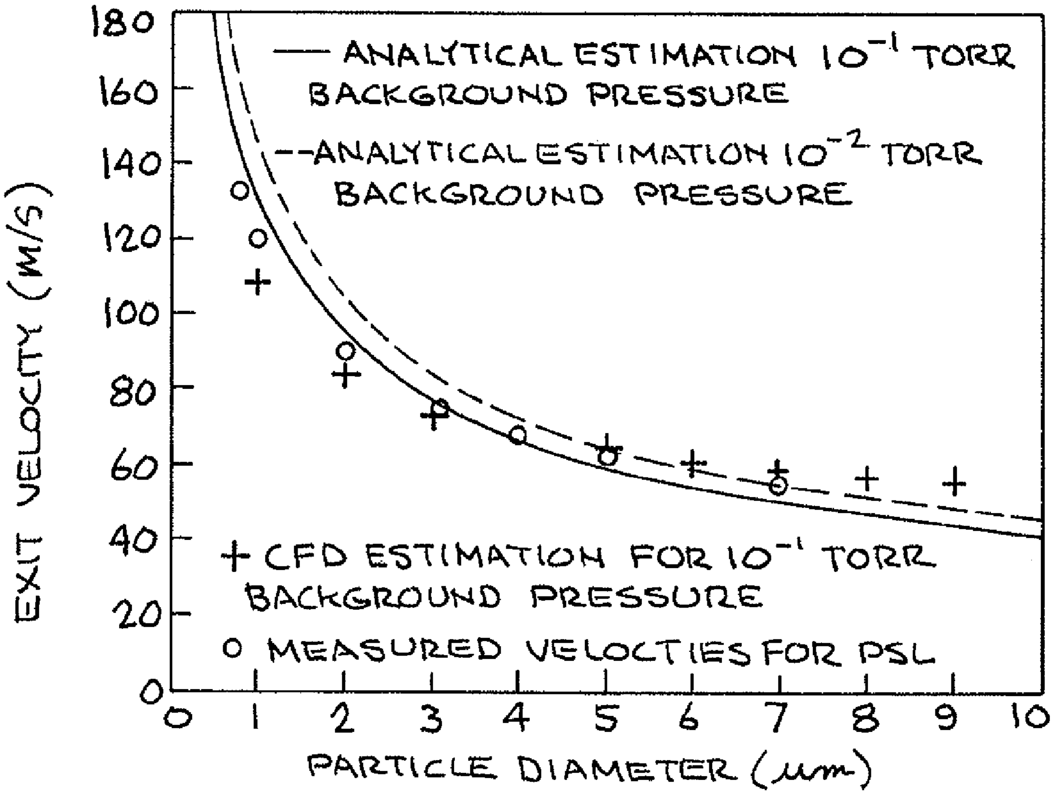
FIG. 16 is a graph showing exit velocities measurement.

Since the particles exiting the focusing device are subsequently tracked and analyzed for chemical composition in a Bio-Aerosol mass spectrometry instrument (BAMS), knowing the particle velocity according to particle aerodynamic diameter is critical. Particle velocities were measured using a 6 laser tracking device developed at Lawrence Livermore National Laboratory for the BAMS instrument. Polystyrene Latex Spheres (PSL) of various calibrated aerodynamic diameters were sent through the focusing inlet and their speed measured. The setup was using a turbo pump split flow in order to reach vacuum after the exit nozzle and a background pressure of $10^{-1}$ Torr. A flat skimmer was then added in order to interface with the tracking system operating at $10^{-4}$ torr. FIG. 16 shows the result compared with analytical predictions computed using the technique described in the theoretical section of this paper and Computational Fluid Dynamic simulations coupled with particle tracking simulations. As can be seen, there is an extremely good agreement between theory, measurement and numerical simulations.

G.4 Focusing and Transmission Performances

Figure 17:
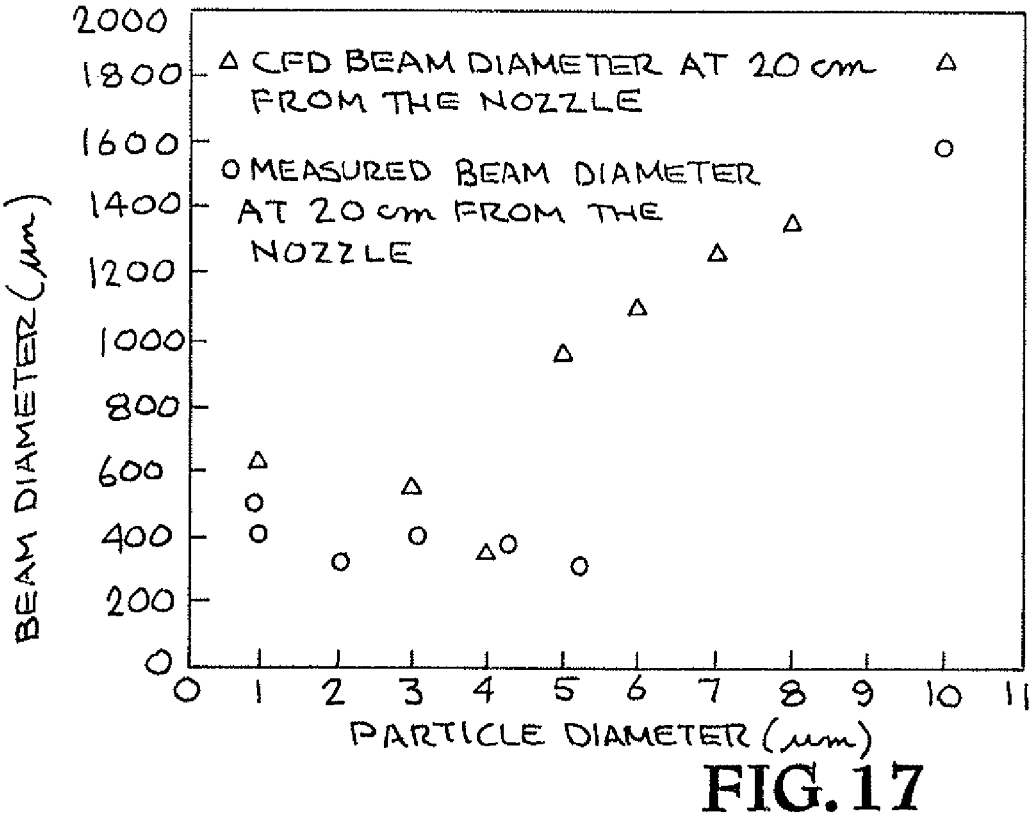
FIG. 17 is a graph showing particle beam diameter at 20 cm from the nozzle of the focusing device.

With regard to size range focusing, the beam size obtained at 20 cm from the tip of the exit nozzle was fairly consistent with results obtained from Computational Fluid Dynamic and particle simulation, as can be seen in FIG. 17. The measurement was performed using size calibrated polystyrene latex spheres. A target coated with grease was located 20 cm below the exit nozzle while particle where sent in high concentration through the device from 10 to 20 min. The particle deposit was then imaged using a microscope and the spot diameter measured afterwards. We tried to measure the beam diameter from the extreme outer edge of the deposit, but, unfortunately, the accuracy of the measurement stays subjective, given that it is somewhat difficult to estimate where the deposit ends. This was even accentuated for large diameter particle where the deposit was fairly faint because the much smaller transmission efficiency and expected beam diameter yield a very low amount of deposited particle per unit area. We must also note that the beam diameter was greatly affected by the pressure in the relaxation chamber especially for the small diameter particles. If the pressure is kept too high above 20 Torr, the 1 um particles are defocused and the beam takes a donut-like shape.

With regard to size range spread and divergence angle, during the testing of this device, it was noticed that the various beam obtained for different particle diameters could be significantly different in location, even though they were well focused. The beam spots on the target for different particle diameters could be as far as 1 mm apart when the different lens orifices are not well aligned. Manual tuning of the location of the individual lenses was able to reduce this issue and maintain the beam center of the focused particles from 1 um to 10 um within 500 um.

Figure 18:
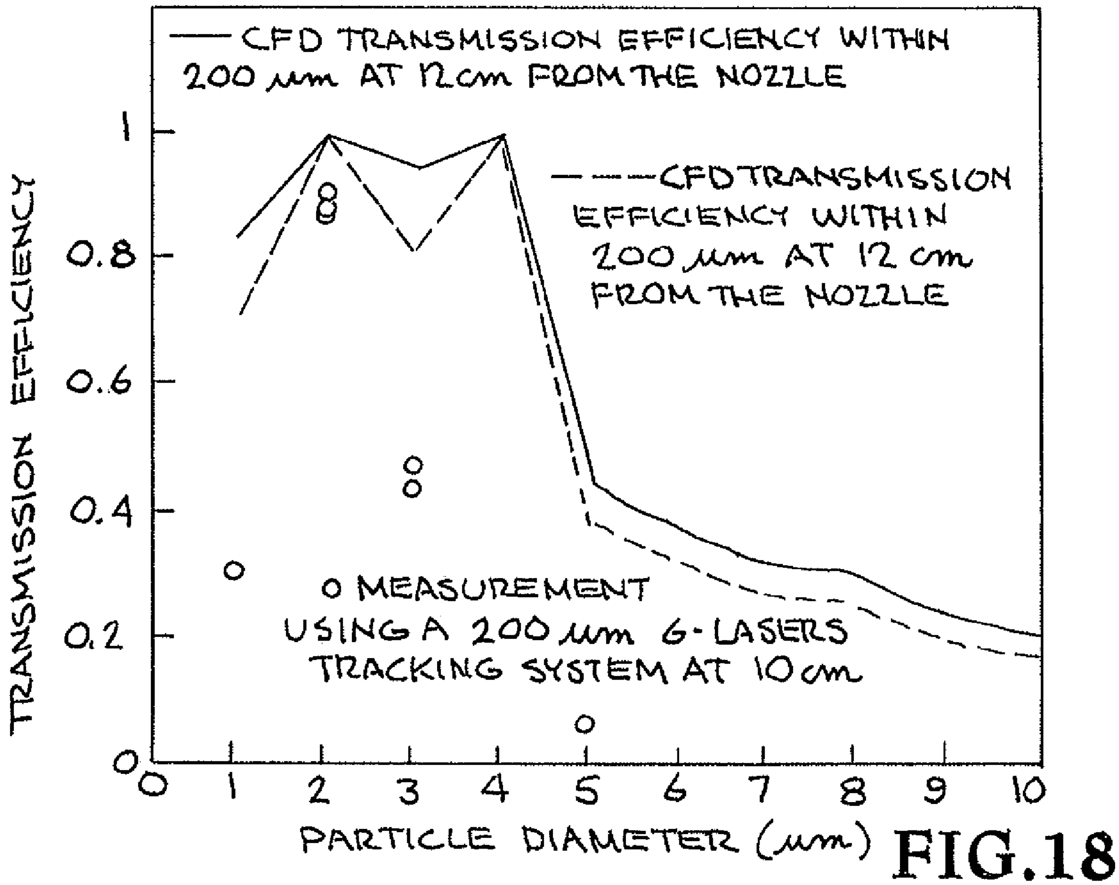
FIG. 18 is a graph showing particle transmission efficiency within 200 um at 10 cm from the nozzle of the focusing device.

With regard to transmission efficiency, in order to measure the transmission efficiency of the full inlet device, the tracking region of the BAMS instrument has been used. This tracking region is using the light scattered from particle when illuminated by 6 Lasers of about 200 um diameter. The lasers span a total distance of 7.5 cm and the first laser is located at 2.5 cm from the exit nozzle of the inlet. This tracking region can then accurately detect and compute each particle speed as long as they are located in a 200 um diameter beam at 10 cm from the exit nozzle. Calibrated PSLs where sent through the system and their concentration was monitored by an Aerodynamic Particle Sizer (APS) spectrometer model 3320 from TSI incorporated. The PFR sampling system was set as described in table 2 and was pulling 1 L/min, thus enabling us to compute the transmission efficiency. Comparatively, Computational Fluid Dynamic computation has been run combined with particle motion in order to estimate the transmission efficiency that should be expected within the 200 um trackable particle beam at 10 cm and 12 cm. FIG. 18 shows the measurement compared with CFD estimation. It must be noted that the alignment of the inlet device with respect to the tracking lasers is crucial and can greatly affect the measured performances. The fact that different particle diameter may have different trajectories and may get focused at different locations affects the measurement as the tracking region of BAMS can only be optimized for one trajectory.

The following references are incorporated in its entirety by reference herein, including:

[1] Tobias, H. J., Kooima, P. M., Dochery, K. S., and Ziemann, P. J. (2000). "Real-Time Chemical Analysis of Organic Aerosols Using a Thermal Desorption Particle Beam Mass Spectrometer," Aerosol Sci. Technol. 33:170-190.

[2] Zhang, X., et al., "A Numerical Characterization of Particle Beam Collimation by an Aerodynamic Lens-Nozzle System Part 1: An Individual Lens or Nozzle," Aerosol Sci Technol., 36, 617-631, 2002.

[3] Liu, P., Ziemann, P. L., Kittelson, D. B., and McMurry, P. H. (1995a). "Generating Particle Beams of Controlled Dimensions and Divergence: I. Theory of Particle Motion in Aerodynamic Lenses and Nozzle Expansions," Aerosol Sci. Technol., 22:293-313.

[4] Schreiner, J., Schild, U., Voigt, C., Mauersberger, K.: "Focusing of aerosols into a particle beam at pressures from 10 to 150 torr.," Aerosol Sci. Technol., 31, 373-382 (1999)

[5] H. Ashkenas and F. S. Sherman, "The structure and utilization of supersonic free jets in low density wind tunnel," International Symposium on Rarefied Gas Dynamics, supp. 3, Vol. 2, pp. 84-105, 1966.

[6] Hinds, W., "Aerosol Technology: Properties, Behavior, And Measurement Of Airborne Particles," Second Edition, Wiley-Interscience, New York, January 1999

[7] Fergenson, D. P.; Pitesky, M. E.; Tobias, H. J.; Steele, P. T.; Czerwieniec, G. A.; Russell, S. C.; Lebrilla, C. B.; Horn, J. M.; Coffee, K. R.; Srivastava, A.; Pillai, S. P.; Shih, M. T. P.; Hall, H. L.; Ramponi, A. J.; Chang, J. T.; Langlois, R. G.; Estacio, P. L.; Hadley, R. T.; Frank, M.; Gard, E. E. "Reagentless Identification of Individual Bioaerosol articles in Milliseconds." Analytical Chemistry 2004, 76, 373-378.

The present invention may be used, for example, for sample identification, climate forcing studies, plume chemistry analysis, meteorology, chemical & bio-warfare agent detection, air & water supply integrity, at office buildings, ports of entry, transportation systems, public events, etc. Additionally, the present invention may also be used, for example, for academic aerosol research, autonomous aerosol pathogen detection systems, etc.

While particular operational sequences, materials, temperatures, parameters, and particular embodiments have been described and or illustrated, such are not intended to be limiting. Modifications and changes may become apparent to those skilled in the art, and it is intended that the invention be limited only by the scope of the appended claims.

We claim:

1. A computerized method for designing an aerodynamic focusing lens stack, said computerized method comprising:

receiving as input in a computer the design parameters of:

(1) the particle size range to be considered ($d_{particle\ (min)}$, $d_{particle\ (max)}$) and the particle density thereof ($\rho_{particle}$); (2) pa characteristics of the gas to be flowed through the aerodynamic focusing lens n stack design, including dynamic viscosity ($\mu$), standard gas mean free path ($\lambda_{standard}$), heat ratio ($\gamma$), gas constant (R), molecular mass (M), and flow type, either isothermal flow or isentropic flow; (3) the temperature (T[1]) and pressure (P[1]) upstream of a first focusing lens [i=1] of the aerodynamic focusing lens stack design; (4) the flow rate through the aerodynamic focusing lens stack equivalent at atmosphere pressure ($Q_{equ}$); and (5) a Stokes number range defining the focusing tightness ($Stk_{min}$, $Stk_{max}$);

based on said received design parameters, determining the number of focusing lenses and their respective orifice diameters ($d_{lens}$[i]) required to focus the particle size range to be considered, and including the steps of:

(a) solving for the orifice diameter ($d_{lens}$[i]) of the $i^{th}$ focusing lens, in the Stokes number equation: FOCUS(T[i], Q[i], P[i], $\lambda_{standard}$, $\mu$, $d_{lens}$[i], $d_{particle}$[i], $\rho_{particle}$, $Stk_{max}$)=0, beginning with the first focusing lens [i=1] where $d_{particle}[1]=d_{particle\ (max)}$ and $$Q[1] = Q_{equ}\left(\frac{P_{atm}}{P[1]}\right);$$

(b) using the value of the orifice diameter ($d_{lens}$[i]) in step (a) to solve for a new maximum particle size $d_{particle}$[i+1] to be focused in the next $[i+1]^{th}$ focusing lens, in the Stokes number equation: FOCUS(T[i], Q[i], P[i], $\lambda_{standard}$, $\mu$, $d_{lens}$[i], $d_{particle}$[i+1], $\rho_{particle}$, $Stk_{min}$)=0;

(c) determining the pressure drop across the $[i]^{th}$ focusing lens by solving for a pressure P[i+1] downstream of the $[i]^{th}$ focusing lens and upstream of the next $[i+1]^{th}$ focusing lens, in the Prandtl derivation: DROP (T[i], Q[i], P[i], P[i+1], $d_{lens}$[i], $\gamma$, R, M)=0;

(d) setting the temperature T[i+1] and flow rate Q[i+1] of the next $[i+1]^{th}$ focusing lens according to: if the flow type is isothermal flow, then $$T[i+1] = T[i] \text{ and } Q[i+1] = Q[i]\left(\frac{P[i]}{P[i+1]}\right) = Q_{equ}\left(\frac{P_{atm}}{P[i+1]}\right);$$

and if the flow type is isentropic flow, then $$T[i+1] = T[i]\left(\frac{P[i+1]}{P[i]}\right)^{\frac{\gamma-1}{\gamma}}$$

and $$Q[i+1] = Q[i]\left(\frac{P[i]}{P[i+1]}\right) = Q_{equ}\left(\frac{P_{atm}}{P[i+1]}\right)^{\frac{1}{\gamma}};$$

and (e) setting i=i+1 and iteratively performing steps (a) through (d) using the values for $d_{particle}$[i+1], P[i+1], T[i+1], and Q[i+1] determined in the previous iteration, until $d_{particle}$[i+1] in step (b) is less than $d_{particle\ (min)}$; and outputting to a designer the respective orifice diameters of all the number of focusing lens determined to be required to focus the particle size range to be considered.

2. The method of claim 1, further comprising:

determining the flow stability through each focusing lens of the aerodynamic focusing lens stack design by solving for the Reynolds number (Re[i]) in the formula:

$$Re[i] = \left(\frac{Q[i]\cdot d_{lens}[i]}{1000\cdot 60\cdot \pi\cdot\left(\frac{d_{lens}[i]}{2}\right)^2}\right)\left(\frac{\rho}{\mu}\right),$$

where $\rho$ is the density of the gas; and outputting to the designer the respective Reynolds numbers of all the number of focusing lens.

3. The method of claim 1, further comprising:

determining the orifice diameter of an exit nozzle of the aerodynamic focusing lens stack design operating in a choked mode to lock the operating pressure and flow, by solving for the orifice diameter ($d_{exitnozzle}$) of the exit nozzle in the Prandtl formula:

$$Q_{exitnozzle} = \pi\left(\frac{d_{exitnozzle}}{2}\right)^2 \cdot \sqrt{\frac{R_0 T_{top}}{M}} \cdot \sqrt{\gamma\left(\frac{2}{\gamma+1}\right)^{\frac{\gamma+1}{\gamma-1}}},$$

where $Q_{exitnozzle}$ is estimated using the formula $$Q_1 = Q_2 \cdot \frac{P_2}{P_1}$$

for the pressure downstream of the last focusing lens, and the pressure downstream of the last focusing lens is itself determined from the final iteration of step (c); and outputting to the designer the orifice diameter of the exit nozzle.

4. A computerized method for designing an aerodynamic focusing lens stack, said computerized method comprising:

receiving as input in a computer the design parameters of: (1) the particle size range to be considered ($d_{particle\ (min)}$, $d_{particle\ (max)}$) and the particle density thereof ($\rho_{particle}$); (2) characteristics of the gas to be flowed through the aerodynamic focusing lens stack design, including dynamic viscosity ($\mu$), standard gas mean free path ($\lambda_{standard}$), heat ratio ($\gamma$), gas constant (R), molecular mass (M), and flow type, either isothermal flow or isentropic flow; (3) the temperature (T[1]) and pressure (P[1]) upstream of a first focusing lens [i=1] of the aerodynamic focusing lens stack design; (4) the flow rate through the aerodynamic focusing lens stack equivalent at atmosphere pressure ($Q_{equ}$); and (5) a Stokes number range defining the focusing tightness ($Stk_{min}$, $Stk_{max}$);

based on said received design parameters, determining the number of focusing lenses and their respective orifice diameters ($d_{lens}$[i]) required to focus the particle size range to be considered, and including the steps of:

(a) solving for the orifice diameter ($d_{lens}$[i]) of the $i^{th}$ focusing lens, in the Stokes number equation: FOCUS(T[i], Q[i], P[i]), $\lambda_{standard}$, $\mu$, $d_{lens}$[i], $d_{particle}$[i], $\rho_{particle}$, $Stk_{max}$)=0, beginning with the first focusing lens [i=1] where $d_{particle}[1]=d_{particle(max)}$ and $$Q[1] = Q_{equ}\left(\frac{P_{atm}}{P[1]}\right);$$

(b) using the value of the orifice diameter ($d_{lens}$[i]) in step (a) to solve for a new maximum particle size $d_{particle}$[i+1] to be focused in the next $[i+1]^{th}$ focusing lens, in the Stokes number equation: FOCUS(T[i], Q[i], P[i], $\lambda_{standard}$, $\mu$, $d_{lens}$[i], $d_{particle}$[i+1], $\rho_{particle}$, $Stk_{min}$)=0;

(c) determining the pressure drop across the $[i]^{th}$ focusing lens by solving for a pressure P[i+1] downstream of the $[i]^{th}$ focusing lens and upstream of the next $[i+1]^{th}$ focusing lens, in the Prandtl derivation: DROP (T[i], Q[i], P[i], P[i+1], $d_{lens}$[i], $\gamma$, R, M)=0;

(d) setting the temperature T[i+1] and flow rate Q[i+1] of the next $[i+1]^{th}$ focusing lens according to: if the flow type is isothermal flow, then $$T[i+1] = T[i] \text{ and } Q[i+1] = Q[i]\left(\frac{P[i]}{P[i+1]}\right) = Q_{equ}\left(\frac{P_{atm}}{P[i+1]}\right);$$

and if the flow type is isentropic flow, then $$T[i+1] = T[i]\left(\frac{P[i+1]}{P[i]}\right)^{\frac{\gamma-1}{\gamma}}$$

and $$Q[i+1] = Q[i]\left(\frac{P[i]}{P[i+1]}\right) = Q_{equ}\left(\frac{P_{atm}}{P[i+1]}\right)^{\frac{1}{\gamma}};$$

and (e) setting i=i+1 and iteratively performing steps (a) through (d) using the values for $d_{particle}$[i+1], P[i+1], T[i+1], and Q[i+1] determined in the previous iteration, until $d_{particle}$[i+1] in step (b) is less than $d_{particle\ (min)}$;

determining the flow stability through each focusing lens of the aerodynamic focusing lens stack design by solving for the Reynolds number $$(Re[i]) \text{ in the formula: } Re[i] = \left(\frac{Q[i] \cdot d_{lens}[i]}{1000 \cdot 60 \cdot \pi \cdot \left(\frac{d_{lens}[i]}{2}\right)^2}\right)\left(\frac{\rho}{\mu}\right),$$

where $\rho$ is the density of the gas;

determining the orifice diameter of an exit nozzle of the aerodynamic focusing lens stack design operating in a choked mode to lock the operating pressure and flow, by solving for the orifice diameter ($d_{exitnozzle}$) of the exit nozzle in the Prandtl formula:

$$Q_{exitnozzle} = \pi\left(\frac{d_{exitnozzle}}{2}\right)^2 \cdot \sqrt{\frac{R_0 T_{top}}{M}} \cdot \sqrt{\gamma\left(\frac{2}{\gamma+1}\right)^{\frac{\gamma+1}{\gamma-1}}},$$

where $Q_{exitnozzle}$ is estimated using the formula $$Q_1 = Q_2 \cdot \frac{P_2}{P_1}$$

for the pressure downstream of the last focusing lens, and the pressure downstream of the last focusing lens is itself determined from the final iteration of step (c); and outputting to a designer the respective orifice diameters of all the number of focusing lens determined to be required to focus the particle size range to be considered, the respective Reynolds numbers of all the number of focusing lens; and the orifice diameter of the exit nozzle.

5. A computer system for designing an aerodynamic focusing lens stack, said computer system comprising:

input means for receiving the design parameters of: (1) the particle size range to be considered ($d_{particle\ (min)}$, $d_{particle\ (max)}$); particle density of the particle size range to be considered ($\rho_{particle}$); (2) characteristics of the gas to be flowed through the aerodynamic focusing lens stack design, including dynamic viscosity (μ), standard gas mean free path ($\lambda_{standard}$), heat ratio (γ), gas constant (R), molecular mass (M), and flow type, either isothermal flow or isentropic flow; (3) the temperature (T[1]) and pressure (P[1]) immediately upstream of a first focusing lens [i=1] of the aerodynamic focusing lens stack design; (4) a flow rate through the aerodynamic focusing lens stack equivalent at atmosphere pressure ($Q_{equ}$); and (5) a Stokes number range defining the focusing tightness ($Stk_{min}$, $Stk_{max}$);

computer processor means for determining, based on said received design parameters, the number of focusing lenses and their respective orifice diameters ($d_{lens}$[i]) required to focus the particle size range to be considered, said computer processor means for determining adapted to:

(a) solve for the orifice diameter ($d_{lens}$[i]) of the $i^{th}$ focusing lens, in the Stokes number equation: FOCUS(T[i], Q[i], P[i], $\lambda_{standard}$, μ, $d_{lens}$[i], $d_{particle}$[i], $\rho_{particle}$, $Stk_{max}$)=0, beginning with the first focusing lens [i=1] where $d_{particle}[1]=d_{particle\ (max)}$ and $$Q[1] = Q_{equ}\left(\frac{P_{atm}}{P[1]}\right);$$

(b) use the value of the orifice diameter ($d_{lens}$[i]) in step (a) to solve for a new maximum particle size $d_{particle}$[i+1] to be focused in the next $[i+1]^{th}$ focusing lens, in the Stokes number equation: FOCUS (T[i], Q[i], P[i], $\lambda_{standard}$, μ, $d_{lens}$[i], $d_{particle}$[i+1], $\rho_{particle}$, $Stk_{min}$)=0;

(c) determine the pressure drop across the $[i]^{th}$ focusing lens by solving for a pressure P[i+1] downstream of the $[i]^{th}$ focusing lens and upstream of the next $[i+1]^{th}$ focusing lens, in the Prandtl derivation: DROP (T[i], Q[i], P[i], P[i+1], $d_{lens}$[i], γ, R, M)=0;

(d) set the temperature T[i+1] and flow rate Q[i+1] of the next $[i+1]^{th}$ focusing lens according to: if the flow type is isothermal flow, then T[i+1]=T[i] and $$Q[i+1] = Q[i]\left(\frac{P[i]}{P[i+1]}\right) = Q_{equ}\left(\frac{P_{atm}}{P[i+1]}\right);$$

and if the flow type is isentropic flow, then $$T[i+1] = T[i]\left(\frac{P[i+1]}{P[i]}\right)^{\frac{\gamma-1}{\gamma}}$$

and $$Q[i+1] = Q[i]\left(\frac{P[i]}{P[i+1]}\right) = Q_{equ}\left(\frac{P_{atm}}{P[i+1]}\right)^{\frac{1}{\gamma}};$$

and (e) set i=i+1 and iteratively performing steps (a) through (d) using the values for $d_{particle}$[i+1], P[i+1], T[i+1], and Q[i+1] determined in the previous iteration, until $d_{particle}$[i+1] in step (b) is less than $d_{particle\ (min)}$; and output means for communicating to a designer the number of focusing lenses and their respective orifice diameters ($d_{lens}$[i]) determined to be required to focus the particle size range to be considered.

6. The computer system of claim 5, further comprising:

computer processor means for determining the flow stability through each focusing lens of the aerodynamic focusing lens stack design by solving for the Reynolds number $$(Re[i]) \text{ in the formula: } Re[i] = \left(\frac{Q[i]\cdot d_{lens}[i]}{1000\cdot 60\cdot\pi\cdot\left(\frac{d_{lens}[i]}{2}\right)^2}\right)\left(\frac{\rho}{\mu}\right),$$

where ρ is the density of the gas; and wherein the output means also communicates to a designer the respective Reynolds numbers of all the number of focusing lens.

7. The computer system of claim 5, further comprising:

computer processor means for determining the orifice diameter of an exit nozzle of the aerodynamic focusing lens stack design operating in a choked mode to lock the operating pressure and flow, by solving for the orifice diameter ($d_{exitnozzle}$) of the exit nozzle in the $$\text{Prandtl formula: } Q_{exitnozzle} = \pi\left(\frac{d_{exitnozzle}}{2}\right)^2\cdot\sqrt{\frac{R_0 T_{top}}{M}}\cdot\sqrt{\gamma\left(\frac{2}{\gamma+1}\right)^{\frac{\gamma+1}{\gamma-1}}},$$

where $Q_{exitnozzle}$ is estimated using the formula $$Q_1 = Q_2\cdot\frac{P_2}{P_1}$$

for the pressure downstream of the last focusing lens, and the pressure downstream of the last focusing lens is itself determined from the final iteration of step (c); and wherein the output means also communicates to a designer the orifice diameter of the exit nozzle.

8. A computer program product comprising:

a computer useable medium and computer readable code embodied on said computer useable medium for causing the automatic determination of an optimal aerodynamic focusing lens stack design based on a set of design parameters, said computer readable code comprising:

computer readable program code means for causing a computer to receive as input the following design parameters: (1) the particle size range to be considered ($d_{particle\ (min)}$, $d_{particle\ (max)}$); particle density of the particle size range to be considered ($\rho_{particle}$); (2) characteristics of the gas to be flowed through the aerodynamic focusing lens stack design, including dynamic viscosity (μ), standard gas mean free path ($\lambda_{standard}$), heat ratio (γ), gas constant (R), molecular mass (M), and flow type, either isothermal flow or isentropic flow; (3) the temperature (T[1]) and pressure (P[1]) immediately upstream of a first focusing lens [i=1] of the aerodynamic focusing lens stack design; (4) a flow rate through the aerodynamic focusing lens stack equivalent at atmosphere pressure ($Q_{equ}$); and (5) a Stokes number range defining the focusing tightness ($Stk_{min}$, $Stk_{max}$);

computer readable program code means for causing the computer to determine, based on said received design parameters, the number of focusing lenses and their respective orifice diameters ($d_{lens}[i]$) required to focus the particle size range to be considered, by:

(a) solving for the orifice diameter ($d_{lens}[i]$) of the $i^{th}$ focusing lens, in the Stokes number equation: FOCUS(T[i], Q[i], P[i], $\lambda_{standard}$, $\mu$, $d_{lens}[i]$, $d_{particle}[i]$, $\rho_{particle}$, $Stk_{max}$)=0, beginning with the first focusing lens [i=1] where $d_{particle}[1]=d_{particle(max)}$ and $$Q[1] = Q_{equ}\left(\frac{P_{atm}}{P[1]}\right);$$

(b) using the value of the orifice diameter ($d_{lens}[i]$) in step (a) to solve for a new maximum particle size $d_{particle}[i+1]$ to be focused in the next $[i+1]^{th}$ focusing lens, in the Stokes number equation: FOCUS(T[i], Q[i], P[i], $\lambda_{standard}$, $\mu$, $d_{lens}[i]$, $d_{particle}[i+1]$, $\rho_{particle}$, $Stk_{min}$)=0;

(c) determining the pressure drop across the $[i]^{th}$ focusing lens by solving for a pressure P[i+1] downstream of the $[i]^{th}$ focusing lens and upstream of the next $[i+1]^{th}$ focusing lens, in the Prandtl derivation: DROP (T[i], Q[i], P[i], P[i+1], $\gamma$, R, M)=0;

(d) setting the temperature T[i+1] and flow rate Q[i+1] of the next $[i+1]^{th}$ focusing lens according to: if the flow type is isothermal flow, then T[i+1]=T[i] and $$Q[i+1] = Q[i]\left(\frac{P[i]}{P[i+1]}\right) = Q_{equ}\left(\frac{P_{atm}}{P[i+1]}\right);$$

and if the flow type is isentropic flow, then $$T[i+1] = T[i]\left(\frac{P[i+1]}{P[i]}\right)^{\frac{\gamma-1}{\gamma}}$$

and $$Q[i+1] = Q[i]\left(\frac{P[i]}{P[i+1]}\right) = Q_{equ}\left(\frac{P_{atm}}{P[i+1]}\right)^{\frac{1}{\gamma}};$$

and (e) setting i+1 and iteratively performing steps (a) through (d) using the values for $d_{particle}[i+1]$, P[i+1], T[i+1], and Q[i+1] determined in the previous iteration, until $d_{particle}[i+1]$ in step (b) is less than $d_{particle\ (min)}$; and computer readable program code means for outputting to a designer the number of focusing lenses and their respective orifice diameters ($d_{lens}[i]$) determined to be required to focus the particle size range to be considered.

9. The computer program product of claim 8, computer readable program code means for causing the computer to determine the flow stability through each focusing lens of the aerodynamic focusing lens stack design by solving for the Reynolds number (Re[i]) in the formula:

$$Re[i] = \left(\frac{Q[i]\cdot d_{lens}[i]}{1000\cdot 60\cdot \pi\cdot\left(\frac{d_{lens}[i]}{2}\right)^2}\right)\left(\frac{\rho}{\mu}\right),$$

where $\rho$ is the density of the gas; and wherein the computer readable program code means for outputting to a designer also provides as output to the designer the respective Reynolds numbers of all the number of focusing lens.

10. The computer program product of claim 8, computer readable program code means for causing the computer to determine the orifice diameter of an exit nozzle of the aerodynamic focusing lens stack design operating in a choked mode to lock the operating pressure and flow, by solving for the orifice diameter ($d_{exit-nozzle}$) of the exit nozzle in the Prandtl formula:

$$Q_{exitnozzle} = \pi\left(\frac{d_{exitnozzle}}{2}\right)^2\cdot\sqrt{\frac{R_0 T_{top}}{M}}\cdot\sqrt{\gamma\left(\frac{2}{\gamma+1}\right)^{\frac{\gamma+1}{\gamma-1}}},$$

where $Q_{exitnozzle}$ is estimated using the formula $$Q_1 = Q_2\cdot\frac{P_2}{P_1}$$

for the pressure downstream of the last focusing lens, and the pressure downstream of the last focusing lens is itself determined from the final iteration of step (c); and wherein the computer readable program code means for outputting to a designer also provides as output to the designer the orifice diameter of the exit nozzle.

* * * * *